(12) United States Patent
Tanaka et al.

(10) Patent No.: US 8,921,052 B2
(45) Date of Patent: Dec. 30, 2014

(54) HEMOGLOBIN DERIVATIVE MEASUREMENT METHOD, AND REAGENT COMPOSITION, MEASUREMENT KIT, ANALYSIS DEVICE AND ANALYSIS SYSTEM FOR USE IN THE METHOD

(75) Inventors: Hirotaka Tanaka, Ehime (JP); Masanori Tanaka, Ehime (JP); Fumihisa Kitawaki, Kanagawa (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 446 days.

(21) Appl. No.: 11/918,394

(22) PCT Filed: Apr. 12, 2006

(86) PCT No.: PCT/JP2006/307781
§ 371 (c)(1),
(2), (4) Date: Nov. 29, 2007

(87) PCT Pub. No.: WO2006/112339
PCT Pub. Date: Oct. 26, 2006

(65) Prior Publication Data
US 2008/0293074 A1    Nov. 27, 2008

(30) Foreign Application Priority Data

Apr. 14, 2005    (JP) .................................. 2005-116870

(51) Int. Cl.
  *G01N 33/53*    (2006.01)
  *C12M 1/00*    (2006.01)
  *G01N 33/72*    (2006.01)

(52) U.S. Cl.
  CPC .............. *G01N 33/72* (2013.01); *G01N 33/721* (2013.01); *G01N 33/5302* (2013.01)
  USPC ........................................ 435/7.1; 435/287.2

(58) Field of Classification Search
  None
  See application file for complete search history.

(56) References Cited

U.S. PATENT DOCUMENTS

| | | | |
|---|---|---|---|
| 3,997,470 A | 12/1976 | Monte et al. .................. | 252/408 |
| 4,658,022 A * | 4/1987 | Knowles et al. .............. | 530/402 |
| 4,970,171 A | 11/1990 | Messenger et al. ............. | 436/66 |
| 5,116,539 A | 5/1992 | Hamaguchi et al. ........ | 252/408.1 |
| 5,151,369 A | 9/1992 | Lewis et al. ..................... | 436/67 |
| 5,258,311 A | 11/1993 | Lewis et al. ..................... | 436/63 |
| 5,420,016 A * | 5/1995 | Boguslaski et al. ............. | 435/12 |
| 5,541,117 A | 7/1996 | Karl et al. ..................... | 436/518 |
| 5,620,690 A * | 4/1997 | Kersten et al. ............. | 424/184.1 |
| 5,707,878 A * | 1/1998 | Tomiyama et al. ........... | 436/520 |
| 5,834,315 A | 11/1998 | Riesgo et al. ................... | 436/66 |
| 6,043,043 A | 3/2000 | Yip .............................. | 435/7.2 |
| 6,117,289 A * | 9/2000 | Yamamoto et al. ...... | 204/403.08 |
| 2002/0173043 A1 | 11/2002 | Merabet et al. ................. | 436/66 |
| 2005/0145490 A1 | 7/2005 | Shinno et al. ............ | 204/403.01 |
| 2005/0158866 A1 | 7/2005 | Xie et al. ......................... | 436/67 |
| 2005/0202399 A1 | 9/2005 | Yonehara et al. ................. | 435/4 |
| 2006/0030050 A1 | 2/2006 | Milne et al. ..................... | 436/67 |

FOREIGN PATENT DOCUMENTS

| | | |
|---|---|---|
| EP | 0 407 860 | 1/1991 |
| EP | 0 849 589 A1 | 6/1998 |
| JP | 1-155268 | 6/1989 |
| JP | 3-51759 | 3/1991 |
| JP | 6-11510 | 1/1994 |
| JP | 2002-340895 | 11/2002 |
| JP | 2005-114359 | 4/2005 |
| JP | 2006-58295 | 3/2006 |
| WO | WO 02/088185 | 11/2002 |
| WO | 03/104815 | 12/2003 |

OTHER PUBLICATIONS

A printout retrieved from http://en.wikipedia.org/wiki/Octyl_glucoside on May 22, 2013.*
A printout retrieved from http://en.wikipedia.org/wiki/List_of_human_blood_components on May 23, 2013.*
Standing, Susan J. et al, "Glycated haemoglobin: an assesssment of high capacity liquid chromatographic and immunoassay methods," *Ann. Clin. Biochem*, Sep. 1, 1992, vol. 29, No. 5, pp. 494-505.

* cited by examiner

*Primary Examiner* — Galina Yakovleva
(74) *Attorney, Agent, or Firm* — Steptoe & Johnson LLP

(57) ABSTRACT

A sample solution including blood components is processed with a denaturalization reagent comprising a nonionic surface-activating agent and an oxidizing agent to denaturalize a hemoglobin derivative in the sample solution, and thereafter, an immunoassay is performing utilizing an antibody that is specific to a denaturalized site of the hemoglobin derivative to measure the amount of the hemoglobin derivative in the sample. Therefore, when performing assay of hemoglobin derivative, denaturalization of hemoglobin can be performed speedily and reliably while minimizing adverse effects of the denaturalization reagent on immune reaction.

8 Claims, 11 Drawing Sheets

-○- Sucrose monocaprate
-△- Sucrose monolaurate
-□- n-Nonyl-β-D-thiomaltoside
-◇- n-Decyl-β-D-maltoside -○- Sucrose monocaprate
-△- Sucrose monolaurate
-□- n-Nonyl-β-D-thiomaltoside
-◇- n-Decyl-β-D-maltoside ○ pepsine
△ Sucrose monocaprate+potassium ferricyanide

Fig.14

|  | sample A | sample B |
|---|---|---|
| concentration of glycated hemoglobin (g/dL) | 0.69 | 0.99 |
| concenctration of hemoglobin (g/dL) | 15.3 | 14.5 |
| ratio of glycated hemoglobin to total hemoglobin (%) | 4.5 | 6.8 |

Fig.15

|  | sample A | sample B |
|---|---|---|
| ratio of glycated hemoglobin to total hemoglobin (%) | 4.5 | 6.7 |

Fig.16

|  | sample A | sample B |
|---|---|---|
| concentration of glycated hemoglobin (g/dL) | 0.68 | 0.97 |
| concenctration of hemoglobin (g/dL) | 15.1 | 14.7 |
| ratio of glycated hemoglobin to total hemoglobin (%) | 4.5 | 6.6 |

HEMOGLOBIN DERIVATIVE MEASUREMENT METHOD, AND REAGENT COMPOSITION, MEASUREMENT KIT, ANALYSIS DEVICE AND ANALYSIS SYSTEM FOR USE IN THE METHOD

The present application is based on International Application PCT/JP2006/307781, filed Apr. 12, 2006, which claimed priority to Japanese Patent Application No. 2005-116870, filed Apr. 14, 2005, the entire contents of which are hereby incorporated by reference.

TECHNICAL FIELD

The present invention relates to a method for measuring hemoglobin derivative in a blood sample, and a reagent composition, a measurement kit, an analysis device and an analysis system which are to be used in the device. More particularly, the invention relates to a technique for denaturalizing hemoglobin speedily and reliably.

BACKGROUND ART

Glycated hemoglobin as one of hemoglobin derivatives is an item that is often measured for early detection of lifestyle diseases, because the glycated hemoglobin enables determination of a blood sugar level in normal condition, excluding an influence of variation in blood sugar due to a meal. The glycated hemoglobin is also referred to as hemoglobin A1c, and it is hemoglobin included in blood erythrocytes, to which glucose is bonded. The glycated hemoglobin is quantified as an abundance ratio of glycated hemoglobin to hemoglobin.

As a glycated hemoglobin measurement method, there is a method utilizing immune reaction. The measurement method utilizing immune reaction is performed as follows. Initially, a blood sample is hemolyzed to extract hemoglobin out of blood erythrocytes. Next, in order to determine whether the hemoglobin is non-glycated hemoglobin or glycated hemoglobin, the cubic structure of the hemoglobin is changed to expose a glycated portion of hemoglobin protein from the cubic structure to the outside (denaturalization of hemoglobin), and further, the glycated portion is reacted with an antibody that specifically recognizes the glycated portion, thereby to immunologically measure the amount of the glycated hemoglobin.

As an example of a hemoglobin denaturalization method, there is a method of denaturalizing hemoglobin with negative ions in a lithium salt form (refer to Patent Document 1). To be specific, in an analysis method for measuring a specific hemoglobin derivative in a blood sample, (a) the blood sample is processed with a dissolution/denaturalization reagent, thereby dissolving blood erythrocytes, and denaturalizing a detectable amount of the derivative which is released from the blood erythrocytes, and (b) a resultant mixed solution is tested by immunoassay with respect to the amount of the denaturalized hemoglobin derivative that exists in the mixture solution. This method uses, as the dissolution/denaturalization reagent, negative ions in a lithium salt form which can dissolve the blood erythrocytes and denaturalize the hemoglobin derivative, and thereby the dissolution and the denaturalization of the hemoglobin derivative can be achieved speedily with the lithium salt concentration that does not significantly interfere with the immunoassay process.

Further, as another denaturalization method, there is a method of denaturalizing hemoglobin with a thiocyanate compound (refer to Patent Document 2). To be specific, this method is an analysis method for measuring a relative amount of a specific hemoglobin derivative in a blood sample, and comprises (a) a process of obtaining a denaturalized blood sample by processing a blood sample with (i) thiocyanate salt that can denaturalize substantially all hemoglobin existing in the blood sample, and has a concentration of 0.5~0.6M in the sample, and (ii) an oxidizing agent that can transform substantially all hemoglobin existing in the blood sample to a form of methemoglobin, (b) a process of quantifying the methemoglobin in the denaturalized blood sample, (c) a process of quantifying a specific hemoglobin derivative in a denaturalized form in the denaturalized blood sample by immunoassay, and (d) a process of associating the test results obtained from the processes (b) and (c).

Furthermore, as still another denaturalization method, there is a method of denaturalizing hemoglobin with an ionic surface-activating agent (refer to Patent Document 3). To be specific, this method is a method for measuring a content of a hemoglobin derivative in a blood sample, and comprises (a) processing a blood sample with a hemolysis reagent including an ionic abluent having a pH of 5~9.5, at a temperature of 4~37° C. for up to ten minutes, and (b) immunologically measuring a hemoglobin derivative in the blood sample in which the hemoglobin derivative is hemolyzed.

Patent Document 1: Japanese Published Patent Application No. Hei. 3-51759
Patent Document 2: Japanese Published Patent Application No. Hei. 1-155268
Patent Document 3: Japanese Published Patent Application No. Hei. 6-11510

DISCLOSURE OF THE INVENTION

Problems to be Solved by the Invention

As described above, there are various methods for denaturalizing hemoglobin, and the respective methods have both merits and demerits. For example, in the method using lithium salt or thiocyanate compound which is disclosed in Patent Document 1 or Patent Document 2, since reagents such as lithium thiocyanate which is most preferable, potassium thiocyanate, and ammonium thiocyanate have very high deliquescent properties, these reagents required careful handling. Further, since these reagents are difficult to keep dry, when they are held in devices or the like, they must be separated from reagents that will be degraded by humidity. Thus, these reagents are subjected to great restrictions in construction methods.

Further, in the method using an ionic surface-activating agent which is disclosed in Patent Document 3, since the strong protein denaturalization effect of the ionic surface-activating agent adversely affects the immune reaction system after the hemoglobin denaturalization process, it is necessary to perform plural stages of operations including diluting the hemoglobin denaturalization solution with a buffer solution or the like, and then mixing the diluted hemoglobin solution with an immune reaction reagent. Such complicated measurement method is inconvenient, and moreover, variation in dilution may cause errors of measured values. Furthermore, the dilution operation makes it difficult to constitute a simple measurement system.

The present invention is made to solve the above-described problems and has for its object to provide a hemoglobin derivative measurement method which can perform denaturalization of hemoglobin speedily and reliably while reducing adverse effect of denaturalization reagents on immune reaction when measuring an amount of hemoglobin derivative, and further, a reagent composition, a measurement kit, an analysis device, and an analysis device which are to be used for the measurement method.

Measures to Solve the Problems

In order to solve the above-mentioned problems, according to the present invention, there is provided a hemoglobin derivative measurement method including a step of processing a sample including blood components with a nonionic surface-activating agent and an oxidizing agent to denaturalize hemoglobin in the sample.

Therefore, a speedy and reliable hemoglobin denaturalization effect can be obtained while minimizing influence on immune reaction.

Further, in the hemoglobin derivative measurement of the present invention, a hemoglobin derivative that is denaturalized by the processing with the nonionic surface-activating agent and the oxidizing agent is detected by performing an immunoassay using an antibody that is specific to a denaturalized site of the hemoglobin derivative.

Therefore, the hemoglobin derivative can be detected.

Further, in the hemoglobin derivative measurement method of the present invention, the hemoglobin derivative is glycated hemoglobin, and the glycated hemoglobin that is denaturalized by the processing with the nonionic surface-activating agent and the oxidizing agent is detected by performing an immunoassay using an antibody that is specific to a denaturalized site of the glycated hemoglobin.

Therefore, the glycated hemoglobin can be detected.

Further, in the hemoglobin derivative measurement method of the present Invention, the sample is processed with the nonionic surface-activating agent having a concentration that does not significantly hinder the immunoassay.

Therefore, a dilution operation is not required after the denaturalization, thereby preventing a reduction in measurement precision due to dilution, and significantly improving user's operability.

Further, the hemoglobin derivative measurement method of the present invention further includes a step of measuring the hemoglobin included in the sample, and an abundance ratio of the hemoglobin derivative to the hemoglobin is calculated.

Therefore, an abundance ratio of the hemoglobin derivative in the sample can be obtained.

Further, the hemoglobin derivative is glycated hemoglobin.

Therefore, an abundance ratio of the glycated hemoglobin in the sample can be obtained.

According to the present invention, there is provided a reagent composition for measuring a hemoglobin derivative in a sample including blood components, which reagent composition includes at least a nonionic surface-activating agent and an oxidizing agent.

Therefore, it is possible to provide a reagent by which a speedy and reliable hemoglobin denaturalization effect can be obtained while minimizing influence on immune reaction.

Further, the reagent composition of the present invention further includes an antibody that is specific to a denaturalized site of the hemoglobin derivative.

Therefore, the hemoglobin derivative can be detected by only mixing the reagent composition and the sample.

Further, in the reagent composition of the present invention, the hemoglobin derivative is glycated hemoglobin, and the reagent composition further includes an antibody that is specific to a denaturalized site of the glycated hemoglobin.

Therefore, the glycated hemoglobin can be detected by only mixing the reagent composition and the sample.

Further, in the reagent composition of the present invention, the nonionic surface-activating agent has a concentration that does not significantly hinder an immunoassay.

Therefore, a dilution operation is not required after the denaturalization, thereby preventing a reduction in measurement precision due to dilution, and significantly improving user's operability.

According to the present invention, there is provided a measurement kit which holds an antibody that is specific to a denaturalized site of the hemoglobin derivative.

Therefore, it is possible to provide a measurement kit by which a speedy and reliable hemoglobin denaturalization effect can be obtained while minimizing influence on immune reaction.

Further, the measurement kit of the present invention holds an antibody that is specific to a denaturalized site of the hemoglobin derivative.

Therefore, the user can easily measure the hemoglobin derivative without having special knowledge.

Further, in the measurement kit of the present invention, the hemoglobin derivative is glycated hemoglobin, and the measurement kit holds an antibody that is specific to a denaturalized site of the glycated hemoglobin.

Therefore, the user can easily measure the hemoglobin derivative without having special knowledge.

Further, in the measurement kit of the present invention, the nonionic surface-activating agent has a concentration that does not significantly hinder the immunoassay.

Therefore, a dilution operation is not required after the denaturalization, thereby preventing a reduction in measurement accuracy due to dilution, and significantly improving user's operability.

According to the present invention, there is provided an analysis device for analyzing a hemoglobin derivative in a sample including blood components, which comprises a sample application part to which at least the sample is applied, a denaturalization part connected to the sample application part, for denaturalizing the hemoglobin derivative in the applied sample with a reagent composition including a nonionic surface-activating agent and an oxidizing agent, and a detection part connected to the denaturalization part, for detecting the denaturalized hemoglobin derivative.

Therefore, it is possible to provide an analysis device which can denaturalize the hemoglobin more easily and speedily.

Further, the analysis device of the present invention further includes an immunoassay part which holds an antibody that is specific to a denaturalized site of the hemoglobin derivative, and the immunoassay part performs an immunoassay using the antibody after the hemoglobin derivative in the sample is denaturalized by the reagent composition, thereby to detect the denaturalized hemoglobin derivative.

Therefore, the hemoglobin derivative in the sample can be detected more easily and speedily by adding the sample as a detection target.

Further, in the analysis device of the present invention, the hemoglobin derivative is glycated hemoglobin, and the device further includes an immunoassay part for holding an antibody that is specific to a denaturalized site of the glycated hemoglobin, and the immunoassay part performs an immunoassay using the antibody after the glycated hemoglobin in the sample is denaturalized by the reagent composition, thereby to detect the denaturalized glycated hemoglobin.

Therefore, the glycated hemoglobin in the sample can be detected more easily and speedily by adding the sample as a detection target.

Further, in the analysis device of the present invention, the nonionic surface-activating agent included in the reagent composition has a concentration that does not significantly hinder the immunoassay.

Therefore, a dilution operation is not required after the denaturalization, thereby preventing a reduction in measurement accuracy due to dilution, and significantly improving user's operability.

Further, the analysis device of the present invention further includes a detection part for detecting hemoglobin included in the sample, which is connected to the sample application part, and an abundance ratio of the hemoglobin derivative to the hemoglobin is calculated.

Therefore, an abundance ratio of the hemoglobin derivative can be obtained more easily and speedily by adding the sample as a detection target.

Further, the hemoglobin derivative is glycated hemoglobin.

Therefore, an abundance ratio of the glycated hemoglobin can be obtained more easily and speedily by adding the sample as a detection target.

According to the present invention, there is provided an analysis system comprising an analysis device, and a measurement unit for measuring the amount of the hemoglobin derivative which is detected at a detection site of the analysis device.

Therefore, it is possible to perform easy and speedy measurement of the hemoglobin derivative, which is hardly affected by user's manual technique.

Effects of the Invention

According to the hemoglobin derivative measurement method of the present invention, since denaturalization of hemoglobin in a sample including blood components is performed by using a nonionic surface-activating agent and an oxidizing agent, the denaturalization can be carried out speedily and reliably.

Further, since the nonionic surface-activating agent has less inhibitory effect on immunoassay when the hemoglobin derivative is measured by immunoassay, a dilution operation for a denaturalization solution is not required, thereby preventing a reduction in measurement accuracy due to variation in dilution. Further, since no dilution operation is required, immunoassay in a simpler form can be constructed.

Further, by measuring the hemoglobin in the sample simultaneously with the hemoglobin derivative, an abundance ratio of the hemoglobin derivative to the hemoglobin can be calculated.

Since the reagent composition of the present invention includes at least a nonionic surface-activating agent and an oxidizing agent, the above-mentioned denaturalization of hemoglobin can be performed speedily and reliably.

Further, the reagent composition may be in any state including a liquid, a solid, and a liquid that is dried. When it is in a solid state, it can be kept in a stable state for long time.

A measurement kit of the present invention holds, in a part thereof, a reagent composition including at least a nonionic surface-activating agent and an oxidizing agent, and the reagent composition and the sample are mixed to denaturalize hemoglobin. Therefore, the denaturalization of hemoglobin can be performed more easily, speedily, and reliably.

Further, since the measurement kit contains reagents required for measurement of hemoglobin derivative, tools for blood collection, and instructions for use, even users having no specific knowledge can easily perform measurement of hemoglobin derivative.

An analysis device of the present invention holds, in a part thereof, at least a nonionic surface-activating agent and an oxidizing agent, thereby providing a device which can perform the above-mentioned denaturalization of hemoglobin speedily and reliably, and removes complicated operations for the users.

Further, the analysis device holds, in a part thereof, an antibody that is specific to a denaturalized site of the hemoglobin derivative, and performs immunoassay by using the antibody after the denaturalization, thereby providing a device which can detect the hemoglobin derivative, and removes complicated operations for the users.

An analysis system of the present invention comprises the above-mentioned analysis device holding the reagents required for measurement of hemoglobin derivative, and a measurement unit for the analysis device only. Therefore, it is possible to perform easy and speedy measurement of hemoglobin derivative, which is hardly affected by manual techniques.

BRIEF DESCRIPTION OF THE DRAWINGS

FIG. 14 is a diagram illustrating hemoglobin concentrations, glycated hemoglobin concentrations, and abundance ratios of glycated hemoglobin, of blood samples A and B according to the second example.

FIG. 15 is a diagram illustrating measurement results of blood samples A and B according to an automatic glycated hemoglobin analyzer of Tosoh Corporation, according to the second example.

FIG. 16 is a diagram illustrating measurement results of blood samples A and B using an analysis system according to a third example of the present invention.

Figure 1:
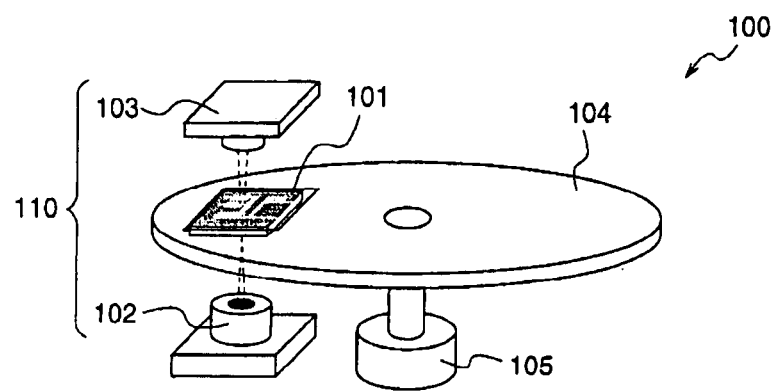
FIG. 1 is a diagram illustrating a construction of an analysis system according to a fourth embodiment of the present invention.

DESCRIPTION OF REFERENCE NUMERALS 100, 300 . . . analysis system
101, 301 . . . analysis device
102 . . . light source
103 . . . detector
104 . . . rotation substrate
105 . . . motor
110, 310 . . . measurement part
201 . . . lower substrate
202 . . . adhesive layer
203 . . . dilution/agitation part
204 . . . dilute solution holding part
205 . . . detection part A
206 . . . detection part B
207 . . . channel
208 . . . quantification part A
209 . . . quantification part B
210 . . . denaturalization reagent
211 . . . latex reagent
212 . . . agglutination reagent
213 . . . upper substrate
215 . . . sample inlet
216 . . . dilute solution inlet
302$a$ . . . upper case
302$b$ . . . lower case
303 . . . latex reagent
304 . . . reagent
305 . . . solution reagent seal
306 . . . inlet
307 . . . case seal
308 . . . light source
309 . . . light receiving part Best Mode To Execute The Invention Hereinafter, embodiments of hemoglobin denaturalization methods according to the present invention will be described in detail.

(Embodiment 1)

According to a first embodiment of the present invention, a description will be given of a hemoglobin derivative measuring method including a step of processing a sample containing blood components with a nonionic surface-activating agent and an oxidizing agent, thereby to denaturalize hemoglobin in the sample.

The above-mentioned hemoglobin (hereinafter also referred to as "Hb") is based on a tetrameric structure which is formed by that α chain globin and non-α chain (β, γ, or δ chain) globin are bonded and associated with heme. About 90% of hemoglobin is HbA($\alpha_2\beta_2$), about 3% is HbA2 ($\alpha_2\delta_2$), and about 1% is HbF($\alpha_2\gamma_2$). As for the HbA, there are HbA0 in which no glucose is bonded to an end of β chain amino acid, and HbA1 in which glucose is bonded thereto. Further, HbA1 includes HbA1a, HbA1b, and HbA1c (hereinafter also referred to as "glycated hemoglobin"), and these glycated HbA1 are called "hemoglobin derivatives".

The point for determining a hemoglobin derivative depends on whether a region where amino-acid residue or peptidic terminus is modified exists or not. For example, the above-mentioned HbA1a has a β chain N terminal being modified with phosphorylated sugar, the HbA1b has a β chain N terminal being aldehyded, and the HbA1c has a β chain N terminal being glycated.

In this way, the hemoglobin derivatives according to the first embodiment are those having different structures of parts of hemoglobin as described above.

There are various kinds of hemoglobin derivatives other than those mentioned above, for example, acetaldehyde-hemoglobin adduct caused by abuse of alcohol, urea-hemoglobin adduct that exists in blood of uremic patients, aspirin-hemoglobin complex, carboxymethylated hemoglobin, and the like.

Although glycated hemoglobin which is generated by a nonenzymatic reaction between reactive amine group of hemoglobin protein and glucose is particularly adopted as an effective measurement item, the measurement item is not restricted thereto.

As described above, in order to measure the hemoglobin derivatives having different structures in only partial regions of hemoglobin, it is necessary to identify and quantify the respective hemoglobin derivatives by distinguishing and recognizing the slightly different regions of the hemoglobin derivatives. In this first embodiment, a process of taking out (expose) the different portions of the hemoglobin derivatives, i.e., the specific portions of the hemoglobin derivatives, from the structure of protein to the outside of the structure is referred to as "denaturalization", and the sites exposed from the structure of protein are referred to as "denaturalized sites".

In this first embodiment, this denaturalization is carried out using a nonionic surface-activating agent and an oxidizing agent.

The denaturalization according to this first embodiment may be performed to an extent that a sub unit structure constituting a quaternary structure is dissociated, or an extent that hydrophobic bonding, hydrogen bonding, van der Waals force, and ion bonding, which constitute a tertiary structure, are dissociated, or an extent that a structure of α helix or β sheet constituting a secondary structure is changed, or an extent that hemoglobin becomes to have a straight-chain structure.

Generally, proteins exist as functional substances within a living body, and this is because the proteins keep accurate steric structures that are formed of the above-mentioned structures. Accordingly, changing the structures leads to changes in the functions of the proteins in no small measure, and thereby the properties of the proteins also change. This change includes both of reduction in function and increase in function.

The nonionic surface-activating agent adopted in this first embodiment is a compound comprising hydrophobic radical having no charge and hydrophilic radical having no charge, and generally it is used for solubilizing a membrane protein. The nonionic surface-activating agent is required to have the following properties. That is, it should have a high solubilization power for a target protein, it should not denaturalize or deactivate the protein, and it should not indicate an inhibitory effect in an activity measurement system such as an immunoassay.

Examples of nonionic surface-activating agents are as follows.

N,N-Bis(3-D-gluconamidopropyl)cholamide (hereinafter denoted as "BIGCHAP")

N,N-Bis(3-D-gluconamidopropyl)deoxycholamide (hereinafter denoted as "deoxy-BIGCHAP")

n-Decyl-β-D-maltopyranoside (hereinafter denoted as "n-Decyl-β-D-maltoside")

n-Dodecyl-β-D-maltopyranoside (hereinafter denoted as "n-Dodecyl-β-D-maltoside")

n-Heptyl-β-D-thioglucopyranoside (hereinafter denoted as "n-Heptyl-β-D-thioglucoside")

n-Octanoyl-N-methylglucamide (hereinafter denoted as "MEGA-8")

n-Nonanoyl-N-methylglucamide (hereinafter denoted as "MEGA-9")

n-Decanoyl-N-methylglucamide (hereinafter denoted as "MEGA-10")

n-Nonyl-β-D-thiomaltopyranoside (hereinafter denoted as "n-Nonyl-β-D-thiomaltoside")

n-Octyl-β-D-glucopyranoside (hereinafter denoted as "n-Octyl-β-D-glucoside")

n-Octyl-β-maltopyranoside (hereinafter denoted as "n-Octyl-β-D-maltoside")

n-Octyl-β-D-thioglucopyranoside (hereinafter denoted as "n-Octyl-β-D-thioglucoside")

β-D-Fructopyranosyl-α-D-glucopyranoside monodecanoate (hereinafter denoted as "Sucrose monocaprate")

β-D-Fructopyranosyl-α-D-glucopyranoside monododecanoate (hereinafter denoted as "Sucrose monolaurate")

Sucrose monocholate

Particularly, the above-mentioned nonionic surface-activating agents for solubilizing membrane proteins are characterized not to denaturalize/deactivate the proteins, and any agent has less denaturalization effect to the protein. However, the inventors of the present invention have discovered that it is possible to aggressively denaturalize hemoglobin by combining nonionic surface-activating agents having the above-mentioned characteristics with oxidizing agents, and selecting an appropriate concentration for each of the obtained reagents (refer to Example 1-(d) described later). Accordingly, in this first embodiment, a blood sample can be denaturalized speedily, reliably, and effectively.

The condition for effectively denaturalizing hemoglobin by the denaturalization reagent of this first embodiment depends on the types of the nonionic surface-activating agents. That is, it depends on the critical micellar concentration (hereinafter referred to as "CMC") of the nonionic surface-activating agent, and hemoglobin is effectively denaturalized at a concentration which is at least higher than the CMC, and more preferably, about twice as high as the CMC, under the existence of the oxidizing agent.

For example, when the CMC of Sucrose monolaurate is 0.02%, hemoglobin can be denaturalized at a concentration of 0.05%. However, when the CMC of Sucrose monocaprate is 0.13%, a concentration of 0.25% or more is required of hemoglobin.

Further, as for the concentration of the oxidizing agent, the oxidizing agent is required to have a concentration for oxidizing all hemoglobin. For example, in order to denaturalize hemoglobin in blood that is diluted to 1/500, 0.1% or more potassium ferricyanide is required (refer to Example 1-(f) described later).

The reason why the denaturalization effect is improved by using the oxidizing agent is because hemoglobin is transformed to methemoglobin by the oxidizing agent and thereby it becomes more likely to be subjected to the denaturalization effect of the nonionic surface-activating agent.

The oxidizing agent may be selected from among substances having charges enough to transform hemoglobin to methemoglobin, and there are $KIO_3$, $KClO_3$, $K_2CrO_4$, $NaNO_2$, $K_3Co(NO_2)_6$ as well as $K_3Fe(CN)_6$ (potassium ferricyanide) that is generally used. However, the oxidizing agent is not restricted these substances, and any substance may be adopted so long as it has a hemoglobin oxidizing property.

In this first embodiment, "processing with a nonionic surface-activating agent and an oxidizing agent" means a process of preparing a nonionic surface-activating agent solution including an oxidizing agent which satisfies the condition for obtaining a desired denaturalization effect, and adding the solution to a sample including a hemoglobin derivative, or adding a blood sample into the nonionic surface-activating agent solution including an oxidizing agent which satisfies the condition for obtaining a desired denaturalization effect. In the case where the blood sample is added to the nonionic surface-activating agent solution, the nonionic surface-activating agent must have not only the denaturalization effect but also an effect of destroying erythrocyte membranes to elute hemoglobin (hemolysis).

Furthermore, the method of processing the sample with the nonionic surface-activating agent also includes a method of directly adding a solid reagent comprising an oxidizing agent and a nonionic surface-activating agent to a sample including a hemoglobin derivative or a blood sample so as to satisfy the condition for obtaining a desired denaturalization effect.

The above-mentioned "solid" reagent may be a "dried" reagent, and the drying method includes air drying, heat drying, vacuum drying, vacuum-freeze drying, etc.

Then, as described above, the sample including the hemoglobin derivative or the blood sample is processed with the nonionic surface-activating agent and the oxidizing agent to denaturalize the hemoglobin derivative in the sample, and thereafter, measurement of the hemoglobin derivative in the sample is performed by using the denaturalized hemoglobin derivative. In this first embodiment, the hemoglobin derivative measuring method includes an immunoassay using an antibody which recognizes an area that is taken out of the structure of hemoglobin by denaturalization, or a method using boric acid having an affinity with cis-diol of glucose.

A great advantage of the hemoglobin derivative measuring method according to the first embodiment is that an immunoassay can be performed utilizing an antibody that is specific to a denaturalized site of the hemoglobin derivative that is processed with the nonionic surface-activating agent and the oxidizing agent, while minimizing adverse effect on an immune reaction. That is, in this first embodiment, since the nonionic surface-activating agent is used in the hemoglobin denaturalization process, a specific area (denaturalized site) that determines the hemoglobin derivative can be taken out of the hemoglobin structure while minimizing adverse effect on the immune reaction. Therefore, more specific measurement can be carried out, and further, steric obstacles are reduced during formation of complexes due to the antigen-antibody reaction, thereby also enhancing the efficiency of the antigen-antibody reaction.

The immunoassay in this first embodiment is a measurement principle based on the antigen-antibody reaction, and it may be any of immunonephelometry, immunonephrometry, latex immunoagglutination, immunoagglutination inhibition, latex immunoagglutination inhibition, fluoroimmunoassay, chemiluminescent immunoassay, electrochemical immunoassay, fluorescence polarization immunoassay, and immunochromatographic assay, which are generally known.

Among the above-mentioned hemoglobin derivatives, glycated hemoglobin is well measured. As a method for measuring glycated hemoglobin, there is adopted an immunoassay utilizing an antibody that is specific to a denaturalized site of the glycated hemoglobin, i.e., a glycated site of the glycated hemoglobin that is exposed to the outside of the hemoglobin structure by denaturalization. The glycated hemoglobin is HbA1c, and it serves as an indicator for managing patients having diabetes which is recently known as one of three major adult diseases, and it provides a measure in long-term glucose control for one to three months. To be specific, HbA1c is reacted with the nonionic surface-activating agent and the oxidizing agent to denaturalize the same and, thereafter, an immunoassay is performed using an antibody that is specific to the glycated site in which amino acid at the β chain N terminal that is specific to HbA1c is glycated.

Generally, in the field of clinical assay, such hemoglobin derivative is obtained as a ratio to the amount of hemoglobin, and therefore, the hemoglobin derivative measuring method includes a step of measuring the amount of hemoglobin included in the sample, a step of measuring the amount of hemoglobin derivative included in the sample, and a step of calculating a ratio of the amount of hemoglobin derivative to the amount of hemoglobin.

The step of measuring the amount of hemoglobin included in the sample may be implemented by a hemoglobin quantification method that is currently well used for clinical examinations, and the hemoglobin quantification method includes a cyanmethemoglobin method, a SLS-hemoglobin method, and a method of measuring absorption of hemoglobin at 415 nm. Alternatively, an immunoassay using an antibody to hemoglobin may be used.

The amount of hemoglobin that is measured in this step is not necessarily be the amount of all hemoglobin included in the sample, which is obtained by completely hemolyzing all erythrocytes, but it may be the amount of partial hemoglobin that is obtained by hemolyzing part of erythrocytes. This is because the amount of hemoglobin derivative is calculated as a ratio to the amount of hemoglobin.

Further, particularly for the case where the hemoglobin derivative is HbA1c, a calculation scheme that is used in the IFCC (International Federation of Clinical Chemistry) reference method may be adopted. That is, it is a method of calculating a ratio of HbA1c to a sum of HbA0 and HbA1c. Hereinafter, the IFCC reference method will be described in detail. Initially, a blood sample is washed with normal saline, and erythrocytes are obtained by centrifugal separation, and then the erythrocytes are incubated at 34° C. for four hours to remove unstable HbA1c. Next, the hemoglobin concentration is adjusted to 6 g/dL, and the sample solution is processed with endprotease and ammonium acetate buffer solution (pH4.0) at 37° C. for eighteen hours. This solution is injected into HPLC, and glycated 6-chain peptide and 6-chain peptide are obtained, and then a peak area is obtained by electrospray ionization.

In this way, a sample including a hemoglobin derivative or a blood sample is processed with a nonionic surface-activating agent and an oxidizing agent to denaturalize hemoglobin, whereby denaturalization of hemoglobin can be speedily and reliably carried out while securing safety.

By the way, when a reagent such as an enzyme or an ionic surface-activating agent is used to denaturalize hemoglobin as in the conventional method, the strong protein-denaturalization effect of the reagent considerably affects the antibody, and particularly, the reagent having a higher concentration is more likely to degrade the antibody activity. Therefore, a stable immunoassay system cannot be constituted. Accordingly, in the conventional method, it is necessary to dilute the hemoglobin derivative solution to a concentration that does not significantly interfere with the immunoassay, after the denaturalization is completed.

However, since the nonionic surface-activating agent used for denaturalization in this first embodiment has less adverse effect on the immunoassay (refer to Example 1-(g) described later), the antibody used for the immunoassay is not significantly denaturalized while the hemoglobin derivative is denaturalized. Consequently, the hemoglobin derivative, the antibody, and the nonionic surface-activating agent can coexist in one measurement system. Therefore, in this first embodiment, one-step measurement that needs no dilution operation is realized, thereby considerably improving the operability.

Among the fifteen types of nonionic surface-activating agents described above, those mentioned below particularly have less adverse effects on the immune reaction (refer to Example 1-(g)).

n-Decyl-β-D-maltoside
MEGA-10
n-Nonyl-β-D-thiomaltoside
Sucrose monocaprate
Sucrose monolaurate Each of these five nonionic surface-activating agents has less adverse effect on the immune reaction even when its concentration is sufficiently high to perform denaturalization of hemoglobin, and the effect on the immune reaction is constant even if the concentration thereof varies. Therefore, it is possible to constitute a very stable immunoassay system.

Of course, even when the nonionic surface-activating agents other than the above-mentioned five nonionic surface-activating agents are used, the adverse effects on the immunoassay system are by far less than that of the conventionally used ionic surface-activating agent, and therefore, a stable immunoassay system can be constituted (refer to Example 1-(h) described later).

As described above, since the hemoglobin derivative measurement method according to the first embodiment includes a step of processing a sample including blood components with a nonionic surface-activating agent and an oxidizing agent to denaturalize hemoglobin in the sample, it is possible to denaturalize the hemoglobin speedily and reliably. Further, since the nonionic surface-activating agent has less inhibitory effect on an immunoassay, when measuring the amount of hemoglobin derivative by an immunoassay reaction after denaturalization, a dilution operation for the solution after the denaturalization is not required, thereby preventing a reduction in measurement precision due to dilution, and improving user's operability.

Furthermore, according to the first embodiment, when the sample including the blood components is processed with the nonionic surface-activating agent and the oxidizing agent, the concentration of the nonionic surface-activating agent is set at a concentration that is equal to or higher than the critical micelle concentration (CMC) of the agent, more preferably, a concentration that is about twice as high as the CMC. Therefore, the hemoglobin denaturalization effect can be further improved.

(Embodiment 2)

Hereinafter, a description will be given of a reagent composition for measuring a hemoglobin derivative, which includes at least a nonionic surface-activating agent and an oxidizing agent, according to a second embodiment of the present invention.

This reagent composition may be in either a liquid state or a solid state, or it may be obtained by drying a liquid-state reagent composition. It is possible to denaturalize hemoglobin by only mixing this reagent composition with a sample solution including hemoglobin. Accordingly, the reagent composition including the nonionic surface-activating agent and the oxidizing agent can be a most fundamental element for easily measuring the hemoglobin derivative.

When using this reagent composition in a solution form, it should be cooled or shielded from light to further improve the stability of the reagent.

The storage stability of the dried reagent composition is generally higher than that of the solution-state reagent composition, and it can be kept for long time.

In order to dry the reagent composition, techniques such as air drying, heat drying, vacuum drying, vacuum-freeze drying, and the like can be adopted. Especially when freeze drying is adopted, it is possible to produce reagent compositions having various designs according to the shapes of containers for freezing the reagent composition. Further, resolvability is further improved by using vacuum-freeze drying.

Further, when the reagent composition includes protein, sugar may be added to the reagent composition to enhance its stability. Further, in order to promote the immune reaction, an immune reaction promoter such as polyethylene glycol may be contained in the reagent composition.

Further, when potassium ferricyanide is used as an oxidizing agent, it should be shielded from light and kept in its dried state to produce a reagent composition that is stable for longer time.

Further, since the nonionic surface-activating agent having extremely small effect on immunoassay is used in this second embodiment, an antibody used for immunoassay and the nonionic surface-activating agent may coexist in a single system, i.e., the reagent composition may include the antibody.

Even when air drying or heat drying is adopted as a method for forming a reagent composition including an antibody, sufficient stability of the reagent composition can be ensured. However, a method using vacuum-freeze drying is most preferable, and the reagent composition can be kept stable. Especially, since the antibody is protein, addition of sugar leads to enhanced stability of the reagent composition.

As described above, according to the second embodiment, since the reagent composition for measuring the hemoglobin derivative includes at least a nonionic surface-activating agent and an oxidizing agent, the above-mentioned denaturalization of hemoglobin can be performed speedily and reliably.

Further, although the reagent composition may be in any of a liquid state, a solid state, and a state obtained by drying a liquid, particularly when it is in a solid state, it can be stored more stably for long time.

Furthermore, when the reagent composition further includes an antibody that is specific to the denaturalized site of the hemoglobin derivative, the hemoglobin derivative can be detected by mixing the reagent composition and the sample, thereby improving user's operability.

(Embodiment 3)

According to a third embodiment of the present invention, a description will be given of a measurement kit which holds a reagent composition including at least a nonionic surface-activating agent and an oxidizing agent, and measures a hemoglobin derivative using the reagent composition.

The measurement kit is an assortment of reagents and members which are required for measurement of a hemoglobin derivative. To be specific, it contains reagents required for measuring a hemoglobin derivative, instructions for use, a blood collecting tool such as a lancet or a syringe, disinfectant goods required before and after blood collection, and weighting tools such as a dispenser and a dropper to be used for application of the reagents. After a sample to be tested is collected, quantitatively diluted, and denaturalized using these reagents and members, the hemoglobin derivative can be easily measured by using an automatic assay device for clinical use or a spectrophotometer.

In the measurement kit, since the processes from denaturalization of the hemoglobin derivative to measurement of the denaturalized hemoglobin derivative are procedurally defined, it is easy to use the measurement kit according to the instructions without the necessity of having specific knowledge. Further, since the reagent required for measuring the hemoglobin derivative is a reagent including at least a nonionic surface-activating agent and an oxidizing agent, denaturalization of the hemoglobin derivative can be carried out speedily and reliably.

Further, the measurement kit may hold an antibody that is specific to the hemoglobin derivative. That is, there is considered a measurement kit comprising a reagent composition including a nonionic surface-activating agent and an oxidizing agent for hemolyzing and denaturalizing hemoglobin, and a reagent for detecting a hemoglobin derivative, which has an antibody that is specific to the denaturalized site of the hemoglobin derivative (when a latex agglutination inhibition reaction is used, a latex labeled antibody and an agglutination reagent as an agglutination multivalent antigen). These reagents are respectively sealed in containers, and the hemoglobin derivative hemolyzing and denaturalizing operation and the immunoassay operation are procedurally defined, thereby realizing more simple measurement of the hemoglobin derivative. While in this third embodiment the latex agglutination inhibition reaction is adopted, any immunoassay reaction may be adopted so long as it can denaturalize hemoglobin, and perform an immunoassay using an antibody that is specific to the denaturalized site of the hemoglobin derivative to measure the amount of the denaturalized hemoglobin derivative.

Further, the reagent composition and the antibody may be separately held in the measurement kit may be, or the antibody may be included in the reagent composition.

Furthermore, a reagent that can measure hemoglobin in the sample may be sealed in a container and included in the measurement kit. Thereby, it is possible to calculate an abundance ratio of the hemoglobin derivative. Calculation of an abundance ratio is effective particularly when measuring glycated hemoglobin.

As a method for measuring hemoglobin, there are proposed a cyanmethemoglobin method and a SLS-hemoglobin method for measuring a peak wavelength around 415 nm or a wavelength around 540 nm by utilizing absorption of hemoglobin itself, and a latex agglutination method.

As described above, since the measurement kit according to the third embodiment contains some or all of reagents required for measuring a hemoglobin derivative in a sample, which are respectively sealed in containers, it is possible for the user to perform hemolysis and denaturalization of hemoglobin, and measure the amount of denaturalized hemoglobin by using a reagent that specifically recognizes the denaturalized hemoglobin derivative, according to a predetermined procedure. Therefore, even when the user has no specific knowledge, he/she can easily perform measurement of the hemoglobin derivative. More preferably, when a reagent that can measure the concentration of hemoglobin in the sample is further added to the measurement kit, an abundance ratio of hemoglobin derivative to hemoglobin can be calculated, which is particularly effective when measuring glycated hemoglobin.

(Embodiment 4)

According to a fourth embodiment of the present invention, a description will be given of an analysis device for analyzing a hemoglobin derivative, which device comprises a sample application part to which at least a sample is applied, a denaturalization part for denaturalizing a hemoglobin derivative in the sample by using a nonionic surface-activating agent and an oxidizing agent, and a detection part for detecting the amount the denaturalized hemoglobin derivative.

The analysis device may be combined with a measurement device for evaluating the analysis device to provide a form of an analysis system. Thereby, measurement of the hemoglobin derivative can be performed more easily and speedily.

The analysis device according to the fourth embodiment holds a nonionic surface-activating agent and an oxidizing agent, and holds a reagent that is specific to a denaturalized site of a hemoglobin derivative, and an agglutination reagents and further, the analysis device may hold these reagents in different parts.

The measurement process includes a denaturalization step of reacting a blood sample with a nonionic surface-activating agent and an oxidizing agent, and a step of reacting the denaturalized hemoglobin derivative with a reagent which is specific to the denaturalized site of the hemoglobin derivative, e.g., a latex-labeled antibody that is obtained by latex-labeling an antibody that is specific to the hemoglobin derivative, and an agglutination reagent.

While the latex-labeled antibody and the agglutination reagent may be simultaneously reacted with the sample solution that is processed by the nonionic surface-activating agent and the oxidizing agent, the sample solution may be initially reacted with the latex-labeled antibody and then reacted with the agglutination reagent.

After the sample solution is reacted with the reagents as described above, variations in absorbance of the reaction solution are measured to calculate the amount of the hemoglobin derivative.

Further, it is possible to calculate an abundance ratio of hemoglobin derivative to hemoglobin by calculating the concentration of hemoglobin in addition to calculating the amount of hemoglobin derivative. As a method for measuring the concentration of hemoglobin, there are proposed a cyanmethemoglobin method and a SLS-hemoglobin method for measuring a peak wavelength around 415 nm or a wavelength around 540 nm by utilizing absorption of hemoglobin itself, and a latex agglutination method.

As for a shape of the analysis device, it is important to smoothly promote the above-mentioned sequence of reactions and measurements.

As an example of the analysis device, for example, a device utilizing centrifugal force and capillary attraction is considered. That is, a liquid sample is freely transferred through plural chambers (spaces) formed in the analysis device and plural channels formed between the chambers, thereby controlling the sequence of measurement, the amounts of reagents, the reaction time, and the like. As an example of a device for evaluating such analysis device, there is proposed a device that is equipped with a rotation mechanism for rotating the analysis device, and an optical measurement function for measuring the absorbance.

Hereinafter, examples of the above-mentioned analysis device and the analysis system including the analysis device will be described with reference to FIGS. 1 and 2.

FIG. 1 is a diagram illustrating the construction of the analysis system. The analysis system 100 comprises an analysis device 101, a measurement unit 110 which irradiates the analysis device 101 with light emitted from a light source 102, and detects transmitted light by a detector 103, a rotation substrate 104, a portion of which is hollowed out, having the analysis device 101 being fixed in the hollow, and a motor 105 for rotating the rotation substrate 104. In FIG. 1, a mechanism for driving the motor 105 and a circuit construction connecting to the light source 102 and the detector 103 are omitted.

Figure 2A:
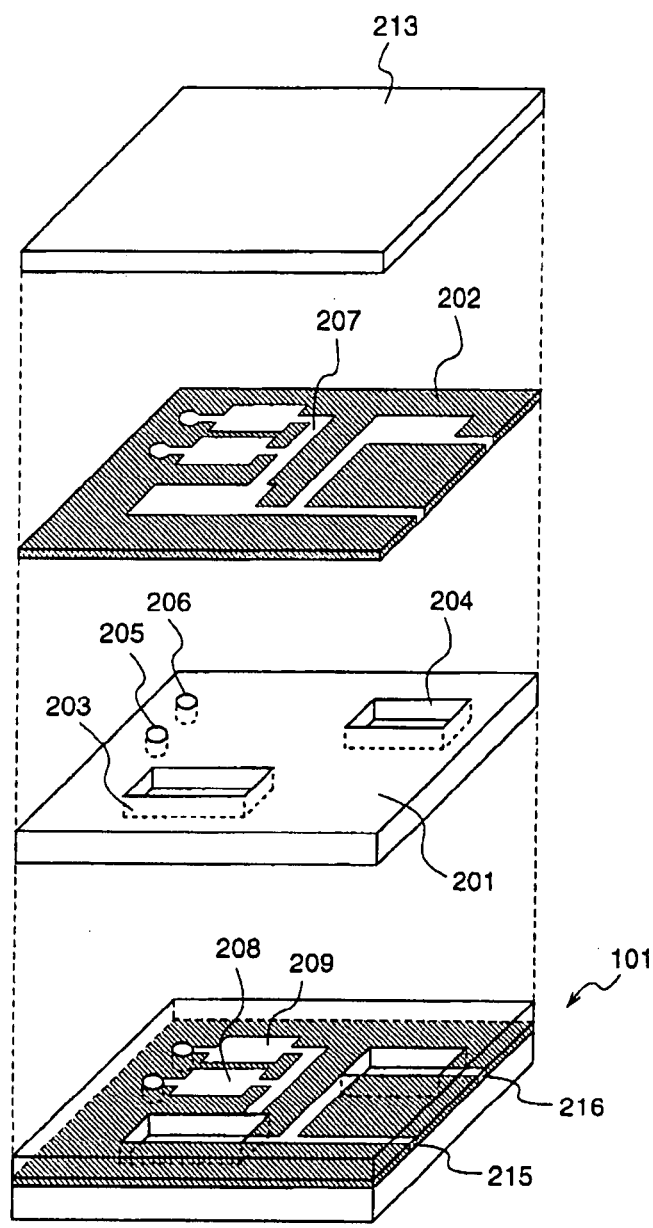
FIG. 2 is a diagram illustrating a specific construction of the analysis device according to the fourth embodiment, wherein FIG. 2($a$) is an exploded perspective view thereof, and FIG. 2($b$) is a perspective view showing a state where a reagent is applied to the analysis device.
Figure 2B:
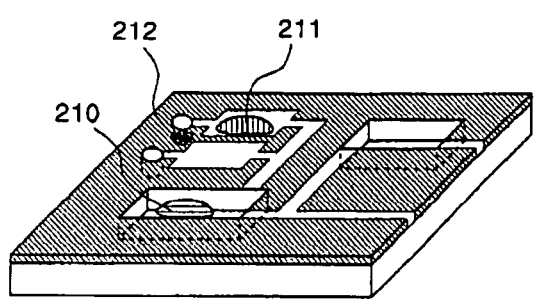

FIG. 2 is a diagram illustrating the specific construction of the analysis device, wherein FIG. 2(a) is an exploded perspective view thereof, and FIG. 2(b) is a diagram illustrating the state where a reagent is applied.

The analysis device 101 comprises a lower substrate 201, an upper substrate 213, and an adhesive layer 202 having adhesive effects on its front and rear surfaces, and the analysis device 101 is formed by bonding these substrates and layer. A transparent resin substrate is used as the lower substrate 201, and spaces of various shapes are accurately formed by injection molding or the like. To be specific, plural concave portions are formed at the upper surface of the lower substrate 201 by injection molding, which concave portions provide a dilution/agitation part 203 that is a denaturalization part for denaturalizing the hemoglobin derivative, a diluted solution holding part 204, a detection part A205 for detecting the amount of added hemoglobin, and a detection part B206 which is a detection part for detecting the amount of denaturalized hemoglobin derivative. Further, any resin may be used as a material of the lower substrate 201 so long as it transmits light. For example, plastic resins such as polycarbonate and polystyrene may be adopted.

Further, on the adhesive layer 202, patterns of the dilution/agitation part 203, the diluted solution holding part 204, the detection part A205, and the detection part B206, and further, patterns of channels 207 connecting these parts are cut out. Further, the channels 207 in front of the detection part A205 and the detection part B206 are cut out so that portions thereof are broadened, thereby forming a quantification part A208 and a quantification part B209 for quantifying the amounts of the solution to be transferred to the detection part A205 and the detection part B206, respectively. As a material for obtaining the adhesion effect of the adhesive layer 202, an adhesive agent or a hot melt sheet which becomes adhesive by heating may be used. The upper substrate 213 comprises a transparent resin plate.

The analysis device 101 is produced as follows. Initially, the lower substrate 201 and the adhesive layer 202 are adhered to each other. Then, before adhering the upper substrate 213 to the adhesive layer 202, as shown in FIG. 2(b), a denaturalization reagent 210 comprising a nonionic surface-activating agent and an oxidizing agent is stored in the dilution/agitation part 203 of the lower substrate 201, and a latex reagent 211 that can specifically react with the denaturalized site of the hemoglobin derivative is stored in the quantification chamber B209 formed by the lower substrate 201 and the adhesive layer 202, and then an agglutination reagent 212 comprising a composite multivalent antigen obtained by combining a plurality of specific epitope structures of the hemoglobin derivative is stored in the detection part B206, respectively. Thereafter, the reagents are dried by vacuum-freeze drying, and the upper substrate 213 is adhered to the upper surface of the adhesive layer 202. Further, two apertures of the channels 207 formed in the adhesive layer 202, which apertures are formed by adhering the upper substrate 213, the adhesive layer 202, and the lower substrate 201, become an analyte injection port 215 and a dilute solution injection port 216, respectively.

Next, the operation of the analysis system 100 will be described.

During analysis of the sample, 1 µL of blood is injected from the analyte injection port 215 of the analysis device 101, and 50 µL of dilute solution is injected from the dilute solution injection port 216, by using a dispenser or the like. Thereby, the blood is stored in the channel inside the analyte injection port 215, and the dilute solution is stored in the dilute solution holding part 204.

Next, the analysis device 101 to which the blood and the dilute solution are injected is set in the hollowed portion of the rotation substrate 104, and the rotation substrate 104 is rotated at a predetermined rpm for a predetermined period of time by the motor 105. Thereby, the dilute solution and the blood are transferred to the dilution/agitation part 203 and mixed with each other to be a diluted sample solution, and hemolysis and denaturalization of the hemoglobin derivative are caused by the functions of the nonionic surface-activating agent and the oxidizing agent.

Next, the rotation of the rotation substrate 104 is stopped, whereby the sample solution is transferred to the quantification part A208 and the quantification part B209 through the channels 207 by capillary phenomenon.

The sample solution transferred to the quantification part B209 is mixed with the latex reagent 211 which has previously been stored in the quantification part B209, whereby the latex reagent 211 and the hemoglobin derivative in the sample solution are combined.

Thereafter, the rotation substrate 104 is again rotated at a predetermined rpm for a predetermined period of time by the motor 105, whereby the sample solution transferred to the quantification part A208 is transferred to the detection part A205, while the sample solution mixed with the latex reagent 211 in the quantification part B209 is transferred to the detection part B206.

The agglutination reagent 212 held in the detection part B206 is combined with the latex reagent that is not combined with the hemoglobin derivative, whereby a latex agglutination inhibition reaction according to the concentration of the hemoglobin derivative occurs. After a predetermined period of time, measurement of transmitted light in the quantification part B206 is executed to detect a latex agglutination inhibition reaction.

Simultaneously, the detection part A205 is measured to measure absorption of hemoglobin, whereby the concentration of hemoglobin can be calculated.

The measurement of the latex agglutination inhibition reaction in the detection part B206 can be performed by measuring the wavelength around 550 nm, and the measurement of hemoglobin in the detection part A205 may be performed by a method of measuring maximum absorption around 415 nm or a method of measuring absorption around 540 nm.

In any case, by previously forming an analytical curve on the basis of hemoglobin of a predetermined concentration and a result of measurement for hemoglobin derivative, the concentrations of hemoglobin and hemoglobin derivative can be respectively calculated using the analytical curve, and further, an abundance ratio of hemoglobin derivative can be calculated by associating the concentration of hemoglobin with the concentration of hemoglobin derivative.

In this fourth embodiment, the analysis system which has the chip-shaped analysis device 101, and controls the sequence of measurements, the amounts of reagents, and the reaction time by fluid transfer utilizing centrifugal force and capillary phenomenon, has been described. However, the present invention is not restricted to the above-mentioned construction and method, and any construction may be adopted so long as it can control the sequence of measurements, the amounts of reagents, and the reaction time. As for the fluid transfer, for example, a method of performing fluid transfer by applying a pressure using a pump is also available. Further, the analysis device may be in a chromatographic form. More simply, even an analysis device in a form of a cubic plastic cell is sufficiently used by devising the reagent holding method.

Hereinafter, a description will be given of an analysis device having a simpler construction, and an analysis system using the analysis device, with reference to FIGS. 3 and 4.

Figure 3:
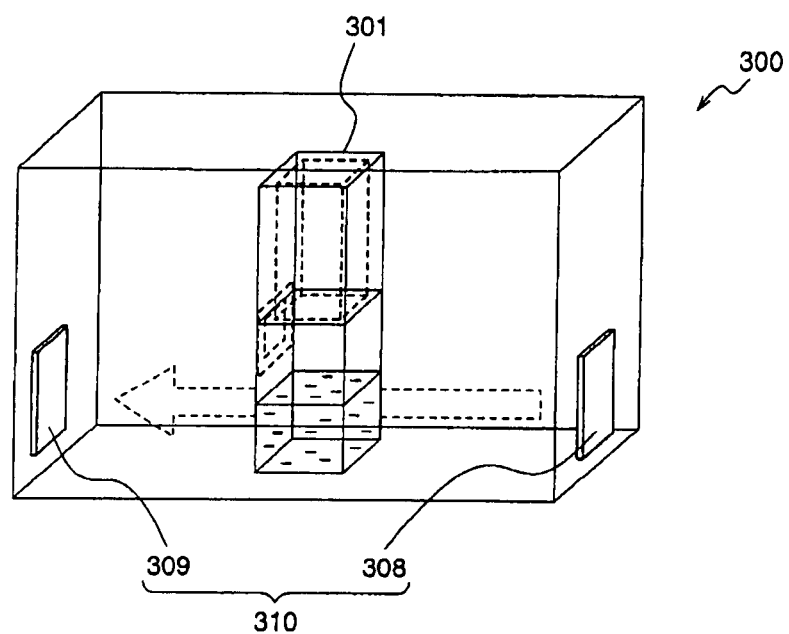
FIG. 3 is a diagram illustrating another construction of the analysis system according to the fourth embodiment.

FIG. 3 is a diagram illustrating another construction of the analysis system according to the fourth embodiment. The analysis system 300 is provided with an analysis device 301, and a measurement part 310 which irradiates the analysis device 301 with light emitted from a light source 308, and detects transmitted light by a light reception part 309. In FIG. 3, a circuit construction for connecting the light source 308 and the light reception part 309, and a structure for setting the analysis device 301 in the analysis system are omitted.

FIG. 4 is a diagram illustrating the specific construction of the analysis device 301, wherein FIG. 4(*a*) is an exploded perspective view thereof, and FIGS. 4(*b*)~4(*d*) are diagrams illustrating the reagent denaturalization procedure in the analysis device 301.

The analysis device 301 comprises a lower case 302*b* having an inlet through which a blood sample is injected, a solution reagent seal 305 for hermetically sealing an opened bottom surface of the lower case 302*b*, an upper case 302*a*, and a case seal 307 for hermetically sealing the inlet 306. The analysis device 301 is formed by adhering the opened bottom surfaces of the upper case 302*a* and the lower case 302*b* with an adhesive agent.

The lower case 302*b* is a rectangular solid case made from plastic, a bottom surface of which is opened, and as shown in FIG. 4(*b*), a reagent 304 which is obtained by adding an antibody that is specific to a denaturalized site of the hemoglobin derivative to a reagent comprising a nonionic surface-activating agent and an oxidizing agent is encapsulated in the lower case 302*b* by the reagent seal 305.

The upper case 302*a* is a rectangular solid case made from plastic, a bottom surface of which is opened, and it is similar in shape to the lower case 302*b*. As shown in FIG. 4(*b*), at an upper end of the case 302*a*, a latex reagent 303 that is able to specifically react with the hemoglobin derivative, which is vacuum-freeze dried, is held at an upper end of the case 302*a*.

Next, the operation of the analysis system 300 will be described.

During analysis of the sample, the reagent 304 comprising the nonionic surface-activating agent, the oxidizing agent, and the agglutination reagent is injected into the lower case 302*b* using a dispenser or the like, and the lower case 302*b* is hermetically sealed with the solution reagent seal 305. Thereafter, as shown in FIG. 4(*b*), the lower case 302*b* and the upper case 302*a* in which the latex reagent is stored are adhered to each other using an adhesive agent. After the solution reagent seal 305 is removed, 0.5 μL of blood sample is injected from the inlet 306 using a dispenser or the like, and the inlet 306 is hermetically sealed with the case seal 307 as shown in FIG. 4(c). Then, the blood sample and the reagent 304 are gently mixed so that the reagent 304 is not applied to the latex reagent 303 that is held at the upper end of the upper case 302a, and the resultant mixture is left for a predetermined period of time. When the concentration of hemoglobin is also to be calculated, the analysis device 301 is set in the analysis system 300 shown in FIG. 3 at this point in time, and an absorbance at 540 nm is measured by the measurement part 310.

Figure 4A:
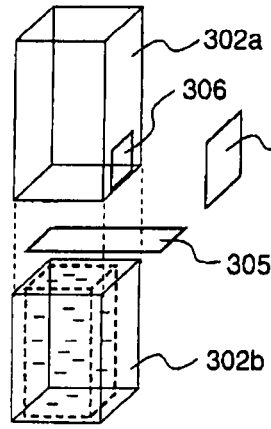
FIG. 4 is a diagram illustrating a specific construction of the analysis device according to the fourth embodiment, wherein FIG. 4($a$) is an exploded perspective view thereof, and FIGS. 4($b$)-4($d$) show a denaturalization procedure to be performed by the analysis device.
Figure 4B:
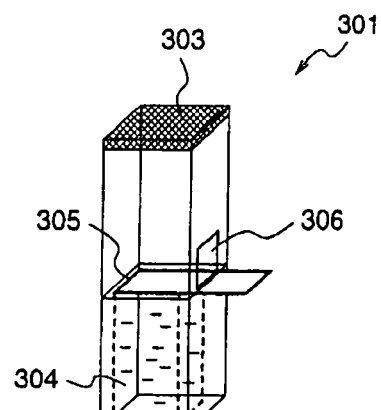
Figure 4C:
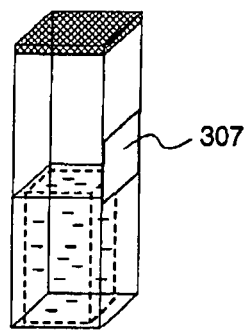
Figure 4D:
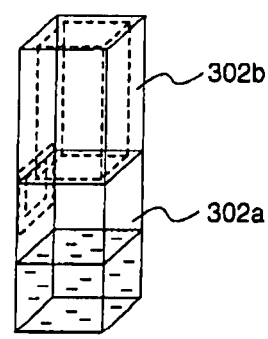

Next, as shown in FIG. 4(d), the analysis device 301 is turned so that the lower case 302b goes upward, whereby the latex reagent 303 is mixed into the reagent 304 to which the blood sample is added, and the resultant mixture is left for a predetermined period of time.

After the predetermined period has passed, the analysis device 301 is set in the analysis system 300 as shown in FIG. 3, and an absorbance at 550 nm is measured by the measurement part 310 to calculate the concentration of hemoglobin derivative.

As described above, according to the fourth embodiment, the analysis device that holds the reagents required for measurement of hemoglobin derivative is designed, and the analysis device is combined with the measurement unit exclusively for the analysis device to constitute the analysis system. Therefore, it is possible to perform easy and speedy measurement of hemoglobin derivative, which is hardly affected by manual procedure.

EXAMPLE 1

Hereinafter, denaturalization effects of various nonionic surface-activating agents will be verified for a case where the hemoglobin derivative is HbA1c which is a representative test item of glycated hemoglobin, and the oxidizing agent to be applied with the nonionic surface-activating agent is potassium ferricyanide.

(a) Preparation of Glycated Hemoglobin Standard Solution (Preparation of Control Solution)

As a kit of reagents for measuring glycated hemoglobin, Cobas reagent HbA1c that is put on the market by Roche Diagnostic K.K. is adopted.

Initially, in order to confirm the responsive property of the glycated hemoglobin to the latex agglutination reagent, dilution sequences of X1, X2, X4, X8, X16, X32, X64, and X128 are produced with respect to a glycated hemoglobin standard solution having a concentration of 24.6 μM which is enclosed in the kit.

(b) Relationship Between Concentration of Glycated Hemoglobin and Amount of Absorption Change Due to Latex Agglutination Inhibition Reaction After 100 μL of 100 kU/L pig-derived pepsine solution is added to each of the 2 μL glycated hemoglobin standard solutions having the respective concentrations (X51 dilution), which are produced in Step(a), the solutions are left for three minutes. Next, 14 μL out of each reaction solution (102 μL) is added into a plastic cell having an optical wavelength of 1 cm, which stores 560 μL of latex reagent solution that can specifically bind to the glycated site of the glycated hemoglobin, and a reaction is promoted for four minutes. Further, 112 μL of composite multivalent glycated hemoglobin antibody having a concentration of 0.5 μg/mL is added to this reaction solution, and an amount of change in absorption at 550 nm is measured three minutes later.

Figure 5:
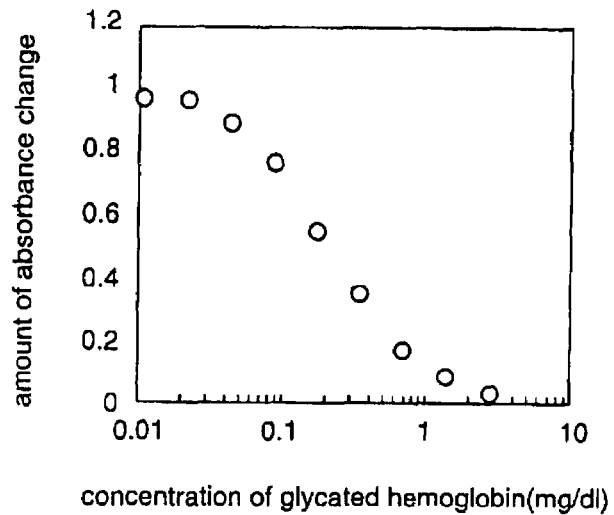
FIG. 5 is a diagram illustrating a control curve which is obtained by processing a standard solution with pig-derived pepsine, according to a first example of the present invention.

FIG. 5 is a diagram in which the concentration of glycated hemoglobin is plotted on the abscissa, while the amount of change in absorption is plotted on the ordinate. In order to convert the concentration of glycated hemoglobin from "mol" to "mg/dL", calculation is performed with the molecular weight of hemoglobin being 64500.

(c) Confirmation of Processing Time Required for Hemoglobin Denaturalization in Control Measurement Method In order to check as to whether all the glycated hemoglobin in the blood is denaturalized and measured by the method of processing the sample with the pig-derived pepsine for three minutes, denaturalization up to 25 minutes is performed to the blood sample, and absorbance values in a latex agglutination inhibition reaction are measured. This operation is performed by the same method as described in Step (b).

Figure 6:
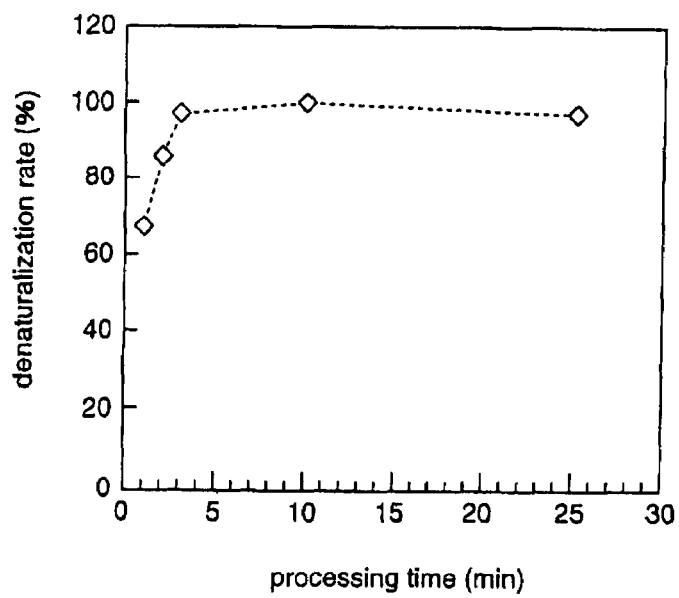
FIG. 6 is a diagram illustrating the relationship between the time for processing a blood sample with pig-derived pepsine, and the hemoglobin denaturalization rate, according to the first example.

FIG. 6 is a diagram in which the processing time of the denaturalization is plotted on abscissa while the hemoglobin denaturalization rate is plotted on the ordinate. The hemoglobin denaturalization rates at the respective processing times are calculated with supposing that the concentration of glycated hemoglobin calculated when the blood sample is processed with the pig-derived pepsine for 25 minutes is 100%.

According to FIG. 6, since there is almost no variation in the calculated concentration of glycated hemoglobin when the processing time exceeds three minutes, it is found that all the hemoglobin is decomposed within three minutes. Accordingly, it is found that all the glycated hemoglobin can be detected by processing the blood sample with the pig-derived pepsine for three minutes, and this is used as a control processing method for the hemoglobin denaturalization test.

(d) Confirmation of Denaturalization Effects of Hemoglobin in Blood with Plural Kinds of Nonionic Surface-Activating Agents The hemoglobin denaturalization effects of the following ten kinds of nonionic surface-activating agents are confirmed.
n-Decyl-β-D-maltoside
n-Dodecyl-β-D-maltoside
n-Heptyl-β-D-thioglucoside
MEGA-8
MEGA-9
MEGA-10
n-Nonyl-β-D-thiomaltoside
n-Octyl-β-D-glucoside
Sucrose monocaprate
Sucrose monolaurate The denaturalization method is as follows. Initially, aqueous solutions (100 μL) respectively including the above-mentioned ten kinds of nonionic surface-activating agents having concentrations ranging from 0.1 to 9% and potassium ferricyanide having a concentration of 0.25% (oxidizing agent) are formed, and 2 μL of blood sample is added to the respective solutions (diluted to X51), and thereafter, the solutions are left for three minutes at 25° C. Next, 14 μL out of each 102 μL reaction solution is reacted with 560 μL of latex reagent solution that is labeled with glycated hemoglobin antibody, for four minutes. Thereafter, the reaction solution is reacted with 112 μL of agglutination reagent, and an amount of change in absorbance at 550 nm is measured three minutes later.

Confirmation of denaturalization is performed as follows. Initially, a concentration of glycated hemoglobin in the blood sample (control value) is calculated from the absorbance value in the latex agglutination inhibition reaction of the same blood sample that is processed with the pig-derived pepsine, and next, concentrations of glycated hemoglobin in the blood are obtained from the absorption values in the latex agglutination inhibition reaction which are obtained when the same blood sample is processed with the above-mentioned ten kinds of nonionic surface-activating agents. Further, what percentages of glycated hemoglobin are detected in the blood samples processed by the respective nonionic surface-activating agents are obtained with respect to the pepsine-processed control, and these percentages are used as denaturalization rates of hemoglobin.

Figure 7:
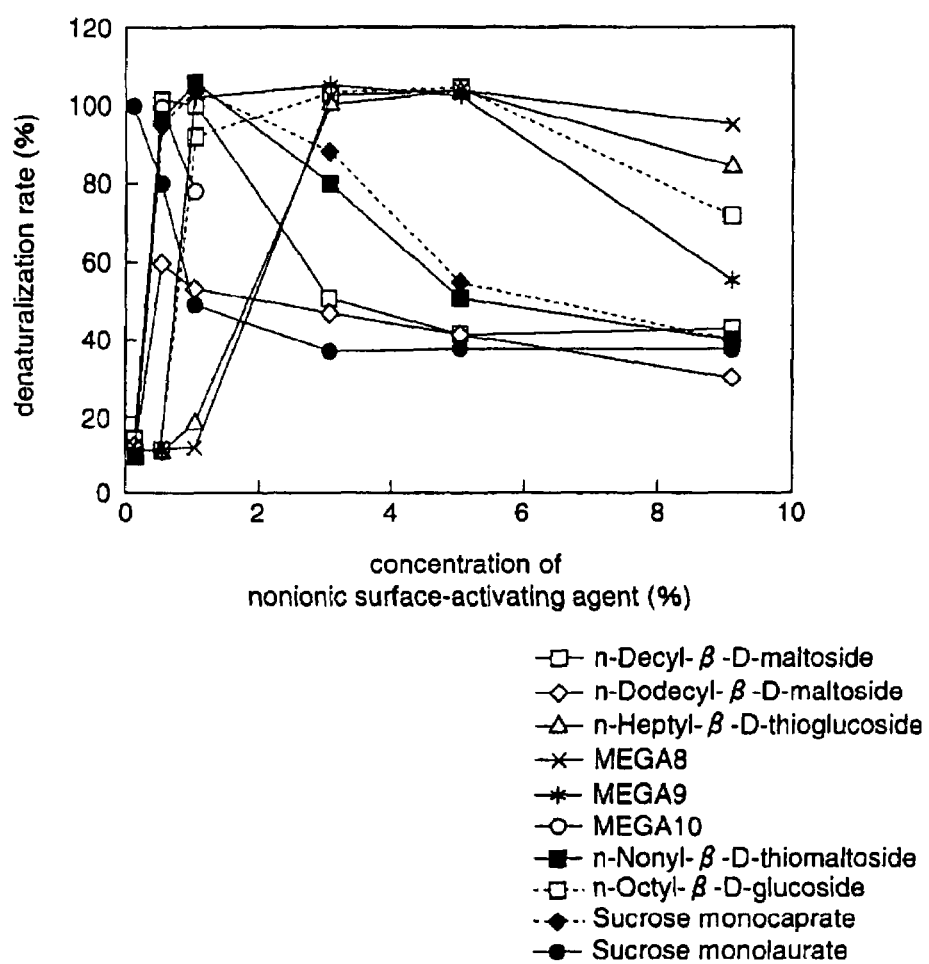
FIG. 7 is a diagram illustrating the relationships between the respective nonionic surface-activating agents and the hemoglobin denaturalization rate, according to the first example.

FIG. 7 is a diagram in which the concentrations of the nonionic surface-activating agents are plotted on the abscissa while the denaturalization rates are plotted on the ordinate.

With reference to FIG. 7, although the nonionic surface-activating agent concentration providing a high denaturalization effect varies depending on the type of the nonionic surface-activating agent, a hemoglobin denaturalization effect as high as that obtained by the pepsine-processing as a control is confirmed for every nonionic surface-activating agent.

(e) Confirmation of Nonionic Surface-Activating Agent Concentration with which the Nonionic Surface-Activating Agent Can Efficiently Denaturalize Hemoglobin in Blood With respect to the following five kinds of nonionic surface-activating agents, the hemoglobin denaturalization effects thereof are confirmed.

Sucrose monocaprate
Sucrose monolaurate
n-Nonyl-β-D-thiomaltoside
n-Decyl-β-D-maltoside The denaturalization method is as follows. Initially, aqueous solutions (1 mL) respectively including the above-mentioned five kinds of nonionic surface-activating agents having concentrations ranging from 0.05% to 0.5% and potassium ferricyanide having a concentration of 0.25% (oxidizing agent) are formed, and 2 µL of blood sample is added to the respective solutions (diluted to X51), and thereafter, the solutions are left for three minutes at 25° C. Next, 140 µL out of each 1002 µL reaction solution is reacted with 560 µL of latex reagent solution that is labeled with a glycated hemoglobin antibody, for four minutes. Thereafter, each reaction solution is reacted with 112 µL of agglutination reagent, and an amount of change in absorbance at 550 nm is measured three minutes later. Confirmation of denaturalization is performed as follows. As described in Step (d), initially, a concentration of glycated hemoglobin in the blood sample (control value) is calculated from the absorbance value obtained in the latex agglutination inhibition reaction of the same blood sample that is processed with pig-derived pepsine, and next, concentrations of glycated hemoglobin in the blood are obtained from the absorption values in the latex agglutination inhibition reaction which are obtained when the same blood sample is processed with the above-mentioned five kinds of nonionic surface-activating agents, and thereafter, denaturalization rates of the respective nonionic surface-activating agents are obtained using the concentration obtained from the pepsine-processed sample as a control.

Figure 8:
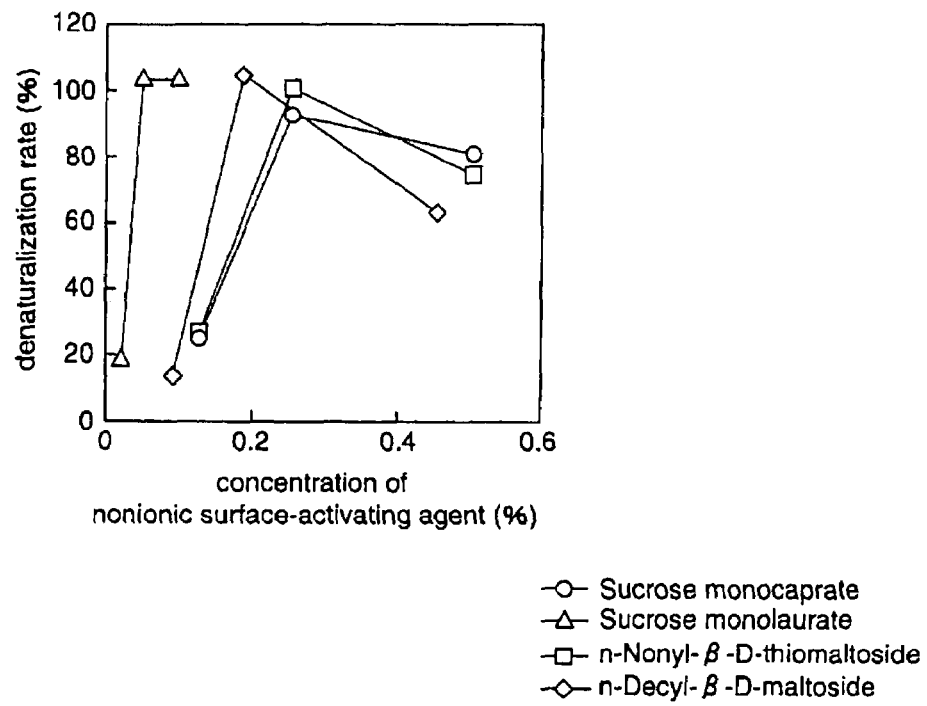
FIG. 8 is a diagram illustrating the relationships between the respective nonionic surface-activating agents and the hemoglobin denaturalization rate, according to the first example.
Figure 9:
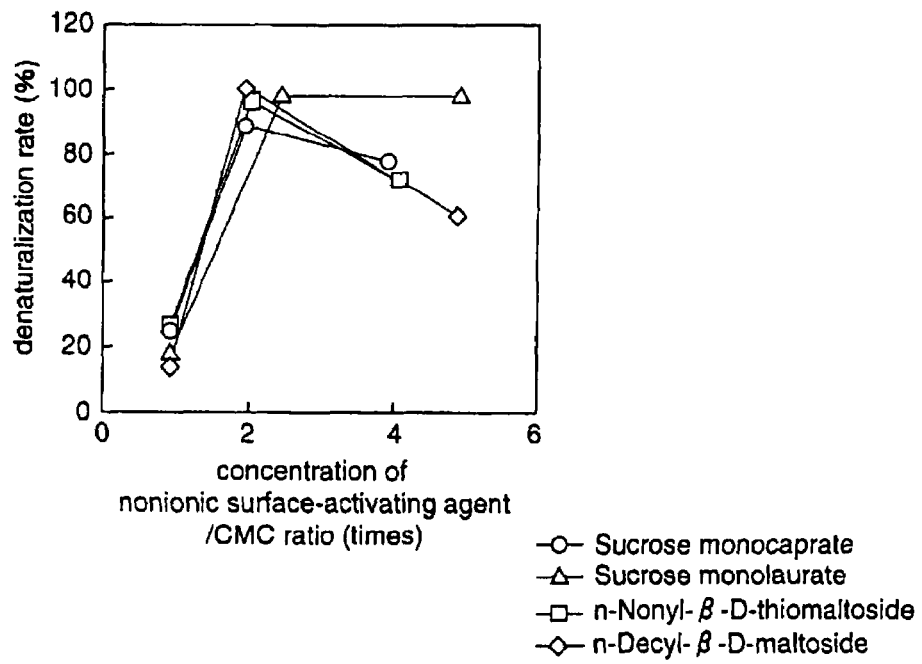
FIG. 9 is a diagram illustrating the relationships between the concentration ratios of the respective nonionic surface-activating agents to CMC, and the hemoglobin denaturalization rate, according to the first example.

FIG. 8 is a diagram in which the concentrations of the nonionic surface-activating agents are plotted on the abscissa while the hemoglobin denaturalization rates are plotted on the ordinate. FIG. 9 is a diagram in which ratios of the CMC (critical micelle concentrations) of the respective nonionic surface-activating agents to the concentrations of the respective nonionic surface-activating agents are plotted on the abscissa, while the glycated hemoglobin denaturalization rates are plotted on the ordinate.

According to FIG. 8, like the result shown in FIG. 7, the nonionic surface-activating agent concentration providing a high hemoglobin denaturalization effect varies depending on the type of the nonionic surface-activating agent. However, as shown in FIG. 9, when the concentrations of the nonionic surface-activating agents to the CMC of the respective nonionic surface-activating agents are checked, it is found that the denaturalization effect is increased at a concentration of each nonionic surface-activating agent that is twice or more as high as the CMC.

(f) Confirmation of Concentration of Oxidizing Agent (Potassium Ferricyanide) which is Required for Denaturalization of Hemoglobin With respect to Sucrose monocaprate which is a nonionic surface-activating agent, a denaturalization effect by potassium ferricyanide is confirmed.

The denaturalization method is as follows. Initially, solutions (1 mL) respectively including potassium ferricyanide of 0, 0.01, 0.05, 0.1, 0.25, and 0.5% with respect to Sucrose monocaprate of 0.5% are prepared, and 2 µL of blood sample is added to the respective solutions (X501 dilution), and thereafter, the solutions are left for three minutes at 25° C.

Next, 140 µL out of each reaction solution (1002 µL) is reacted with 560 µL of latex reagent solution which is labeled with a glycated hemoglobin antibody, for four minutes. Thereafter, the reaction solution is reacted with 112 µL of agglutination reagent, and an amount of change in absorbance at 550 nm is measured after three minutes. In this test, the hematocrit value (Hct) of the blood sample is adjusted to 20, 45, and 70%.

Confirmation of denaturalization is performed as follows. As in the above-mentioned step (d), initially a concentration of glycated hemoglobin in the blood sample is calculated from the absorbance value (control value) obtained in the latex agglutination inhibition reaction of the blood sample that is processed with pig-derived pepsine, and next, a concentration of glycated hemoglobin in the blood is obtained from the absorption value in the latex agglutination inhibition reaction which is obtained when the same blood sample is processed with the nonionic surface-activating agent. Then, what percentage of glycated hemoglobin is detected in the blood sample processed by the nonionic surface-activating agent is obtained with respect to the pepsine-processed control, and this percentage is used as a hemoglobin denaturalization ratio.

Figure 10A:
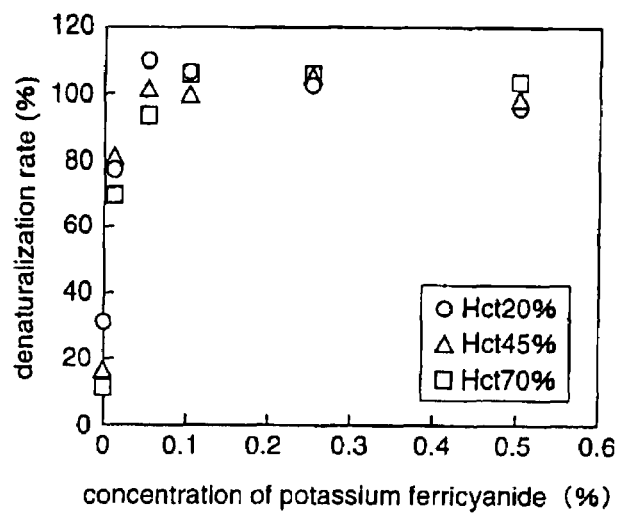
FIG. 10($a$) is a diagram illustrating the relationship between the respective potassium ferricyanide concentrations and the hemoglobin denaturalization rate according to the first example, and FIG. 10($b$) is a diagram illustrating the relationship between the ratio of the amount of potassium ferricyanide to the amount of hemoglobin, and the hemoglobin denaturalization rate, according to the first example.
Figure 10B:
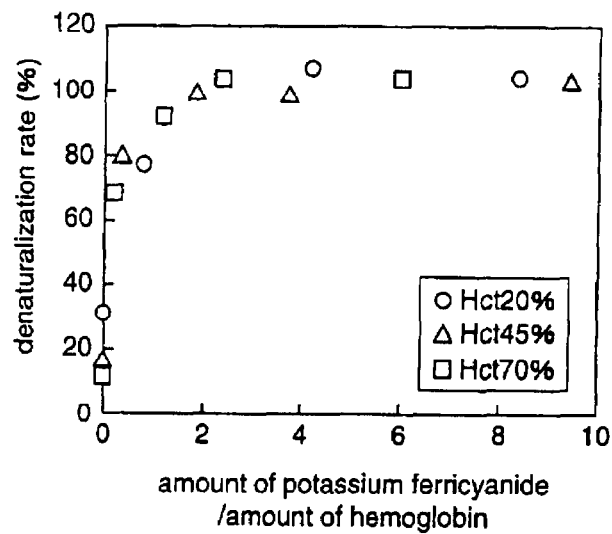

FIG. 10(a) is a diagram wherein the concentration of potassium ferricyanide is plotted on the abscissa while the hemoglobin denaturalization rate is plotted on the ordinate, and FIG. 10(b) is a diagram wherein the ratio of the amount of potassium ferricyanide to the amount of hemoglobin is plotted on the abscissa while the hemoglobin denaturalization rate is plotted on the ordinate.

According to FIG. 10(a), it is found that, although the hemoglobin denaturalization effect is poor with the nonionic surface-activating agent alone, sufficient denaturalization can be achieved by processing the blood sample using 0.1% or more of potassium ferricyanide as well as the nonionic surface-activating agent, even when the blood sample has a hematocrit value of 70%.

Further, according to FIG. 10(b), it is evident that all the hemoglobin in the blood can be denaturalized when the amount of potassium ferricyanide is twice or more than the amount of hemoglobin, and thereby it is found that the existence of potassium ferricyanide is deeply engaged with the denaturalization of hemoglobin.

(g) Confirmation of Influence of Nonionic Surface-Activating Agent on Latex Agglutination Reaction (Immunoassay Reaction)

Influences of the following nine kinds of nonionic surface-activating agents on latex agglutination reaction are confirmed.

n-Decyl-β-D-maltoside
n-Heptyl-β-D-thioglucoside
MEGA-8
MEGA-9
MEGA-10
n-Nonyl-β-D-thiomaltoside
n-Octyl-β-D-glucoside
Sucrose monocaprate
Sucrose monolaurate The denaturalization method is as follows. The respective nonionic surface-activating agent solutions are added to the above-mentioned latex reagent solution, and then the agglutination agent is added. Three minutes later, an amount of change in absorbance at 550 nm is measured for each solution.

Confirmation of influence on immunoassay reaction is performed as follows. An absorbance change amount in the latex agglutination reaction which is obtained when each nonionic surface-activating agent is added so that its final concentration becomes about 0.25~1.4% is compared with an absorbance change amount in the latex agglutination reaction which is obtained when no nonionic surface-activating agent is added.

Simultaneously, as for sodium lauryl sulfate (SLS) which is an ionic surface-activating agent disclosed in Patent Document 3, its influences on latex agglutination reaction at the concentrations of 0.1% and 0.25% are confirmed.

Figure 11:
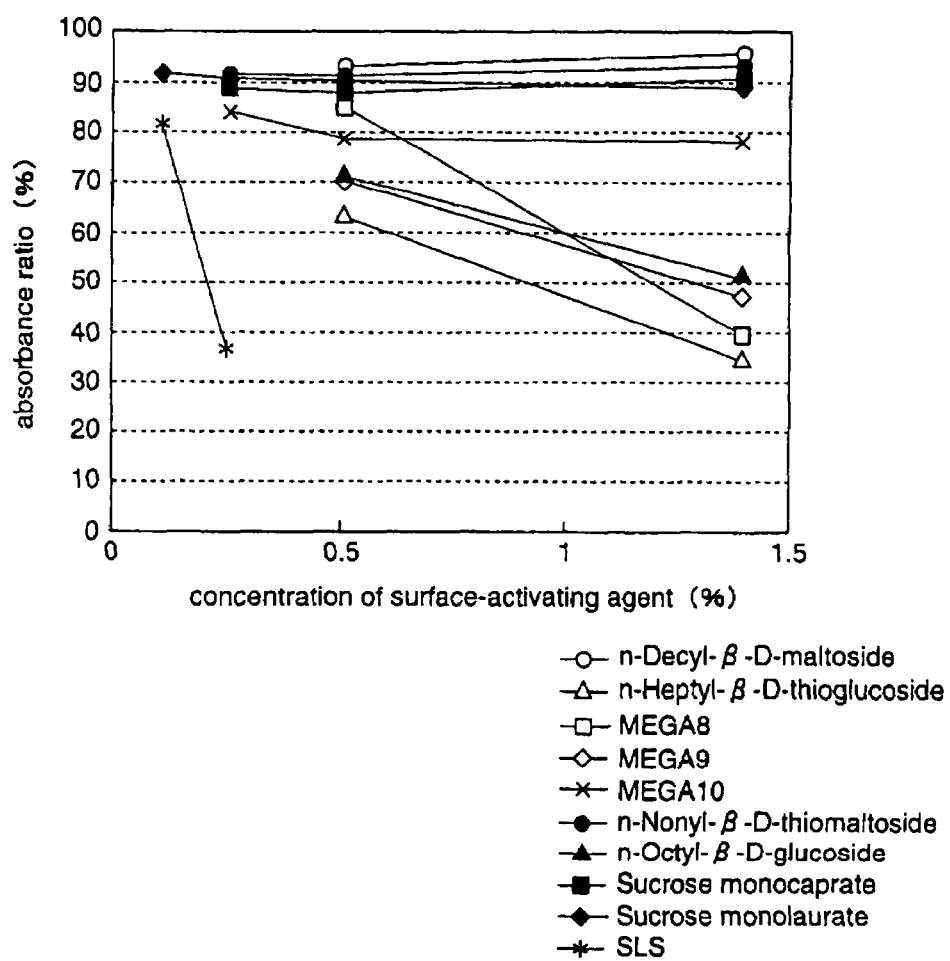
FIG. 11 is a diagram for explaining adverse effects of the respective nonionic surface-activating agents and ionic surface-activating agents on latex agglutination reaction, according to the first example.

FIG. 11 is a diagram in which the concentrations of the respective nonionic surface-activating agents are plotted on the abscissa, while the absorbance change amount ratios of the respective nonionic surface-activating agents when the absorbance change amount of the control is 100% are plotted on the ordinate.

According to FIG. 11, it is found that, while sodium lauryl sulfate (SLS) as an ionic surface-activating agent shows an extreme downward tendency of the latex agglutination reaction with an increase in its concentration, the influences of the nonionic surface-activating agents on the latex agglutination reaction are gentle.

Further, it is confirmed that, amongst the nonionic surface-activating agents, particularly n-Decyl-β-D-maltoside, n-Nonyl-β-D-thiomaltoside, MEGA-10, Sucrose monocaprate, and Sucrose monolaurate have less influences on the latex agglutination reaction even when the concentrations thereof provide sufficient hemoglobin denaturalization effect. This result suggests that the hemoglobin denaturalization solution can be sufficiently used as a reagent composition for latex agglutination reaction or a reagent composition for latex agglutination inhibition reaction.

(h) Confirmation of Effect of Latex Agglutination Inhibition Reaction (Immunoassay Reaction) Under Existence of Nonionic Surface-Activating Agent Three kinds of blood samples having different glycated hemoglobin concentrations are prepared.

Initially, 100 µL of 100 kU/L pig-derived pepesine solution is added to 2 µL of blood (X51 dilution), and the solution is processed for three minutes. Then, 14 µL out of this 102 µL reaction solution is added to a plastic cell which has an optical path length of 1 cm and contains 560 µL of latex labeled antibody solution that can specifically bind to a glycated site of glycated hemoglobin, and reaction is promoted for four minutes. Further, 112 µL of 0.5 µg/mL composite multivalent glycated hemoglobin antibody is added to this reaction solution, and an amount of change in absorbance at 550 nm is measured three minutes later. The same experiment is performed to the blood samples of the respective concentrations.

Next, 100 µL of 0.5% Sucrose monocaprate and 0.25% potassium ferricyanide solution is added to 2µL of blood, and this solution is processed for three minutes. Then, 14 µL out of this 102 µL reaction solution is added to a plastic cell which has an optical path length of 1 cm and contains a latex reagent that can specifically bind to a glycated site of glycated hemoglobin, and 0.5% Sucrose monocaprate, and a 0.25% potassium ferricyanide solution, and reaction is promoted for four minutes. Further, 112 µL of 0.5 µg/mL composite multivalent glycated hemoglobin antibody is added to this reaction solution, and an amount of change in absorbance at 550 nm is measured three minutes later. As in the case of using pepsine, the same experiment is performed to the blood samples of the respective concentrations.

Figure 12:
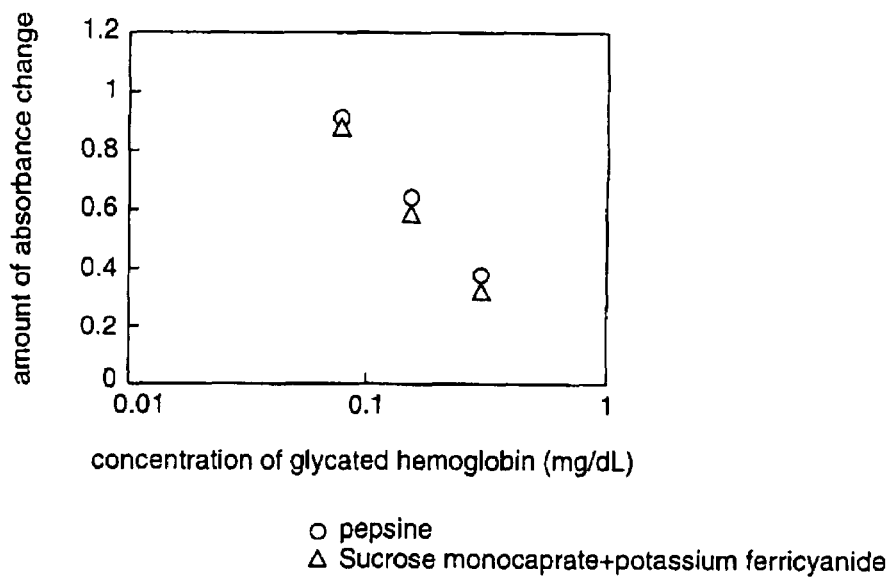
FIG. 12 is a diagram illustrating a measurement result obtained when glycated hemoglobin is denaturalized and subjected to latex agglutination inhibition reaction, which is compared with a measurement result obtained by the conventional method, according to the first example.

FIG. 12 is a diagram in which the glycated hemoglobin concentration is plotted on the abscissa while the absorbance change amount is plotted on the ordinate.

According to FIG. 12, since the absorbance according to the glycated hemoglobin concentration is obtained, it is found that denaturalization reaction of hemoglobin derivative can be performed by the 0.5% Sucrose monocaprate and 0.25% potassium ferricyanide solution, and latex agglutination inhibition reaction can be performed in the state where the denaturalization reagent composition is included.

EXAMPLE 2

Hereinafter, a method for measuring an abundance ratio of hemoglobin derivative is verified.

(a) Measurement of Control for Hemoglobin Concentration

Measurement of hemoglobin adopts "Hemoglobin B-test Wako" which is put on the market by Wako Pure Chemical Industries Ltd. This is a method for detecting hemoglobin by an SLS-hemoglobin method.

Initially, creation of a standard curve of hemoglobin is carried out in the following procedure.

Figure 13:
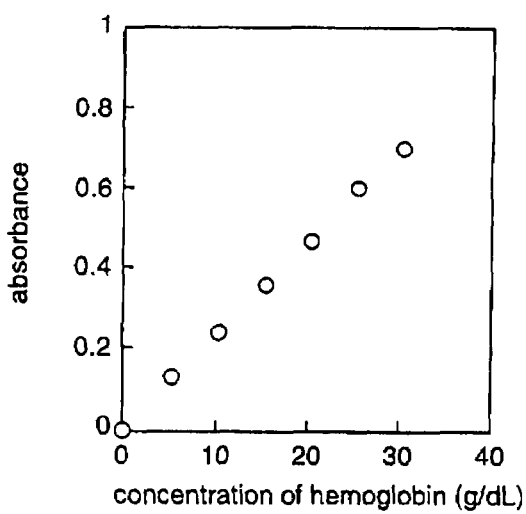
FIG. 13 is a diagram for explaining a hemoglobin measurement result obtained in measurement using "Hemoglobin B-test Wako", according to the second example.

Reaction solutions are produced by adding hemoglobin standard solutions of 5 g/dL, 10 g/dL, and 15.0 g/dL, each by 20 µL, to 5 mL of 3.5 mM sodium lauryl sulfate solution, and a reaction solution is produced by adding 40 µL of 15.0 g/dL hemoglobin standard solution to 5 mL of 3.5 mM sodium lauryl sulfate solution, and then absorbances at 540 nm are measured in a cell having an optical path length of 1 cm. FIG. 13 a diagram in which the hemoglobin concentration is plotted on the abscissa while the absorbance is plotted on the ordinate, with the hemoglobin concentration of the reaction solution to which 40 µL of 15 g/dL hemoglobin standard solution is added being 30 g/dL, and this is used as a control for hemoglobin concentration measurement.

(b) Calculation of Abundance Ratio of Glycated Hemoglobin

Next, blood samples A and B as measurement targets are added each by 20 µL to 5 mL of 3.5 mM sodium lauryl sulfate solution. Then, an absorbance at 540 nm of this reaction solution is measured, and hemoglobin concentrations of the blood samples A and B are obtained from the absorbance data of the already-known hemoglobin concentrations shown in FIG. 13. Next, each of the 2 µL blood samples A and B is added to 100 µL of a 0.5% Sucrose monocaprate/0.25% sodium lauryl sulfate solution, and the solution is left for three minutes. Next, 14 µL out of the 102 µL reaction solution is reacted with 560 µL of latex solution that is labeled with a glycated hemoglobin antibody, for four minutes. Thereafter, the solution is reacted with 112 µL of agglutination reagent, and an amount of change in absorbance at 550 nm is measured three minutes later.

FIG. 14 is a diagram illustrating the hemoglobin concentrations, the glycated hemoglobin concentrations, and the ratios of glycated hemoglobin to total hemoglobin, of the blood samples A and B, respectively.

Further, FIG. 15 shows the result of measurement for the ratios of glycated hemoglobin in the above-mentioned blood samples A and B, by using an automatic glycated hemoglobin analyzer (HLC-723 GHbV) of Tosoh Corporation, which provides a standard method for glycated hemoglobin measurement.

When FIGS. 14 and 15 are compared, it is found that the results of very high correlations are obtained. It is suggested that sufficient denaturalization of hemoglobin is performed by processing the blood samples with the 0.5% Sucrose monocaprate/0.25% sodium lauryl sulfate solution, and thereby glycated hemoglobin concentrations can be calculated.

While in this second example the experimental result is shown only for the case where the nonionic surface-activating agent is Sucrose monocaprate, the same result as mentioned above can be achieved with other nonionic surface-activating agents having denaturalization effects.

EXAMPLE 3

Hereinafter, measurement of hemoglobin derivative using an analysis system shown in FIG. 3 will be described.
(a) Formation of Analysis Device Initially, as shown in FIG. 4(b), a latex reagent 303 comprising a solution that includes a latex reagent that can specifically bind to glycated hemoglobin and 5% sucrose is held by vacuum-freeze drying, at an upper end of a plastic upper case 302a having a length of 0.5 cm, a width of 0.5 cm, and a height of 1 cm, a bottom surface of which is opened, as shown in FIG. 4(a).

Next, as shown in FIG. 4(b), 0.2 mL of solution comprising 0.5% Sucrose monocaprate and 0.25% potassium ferricyanide, and a composite multivalent glycated hemoglobin antibody are injected as a reagent 304 into a plastic lower case 302b having the same configuration as the upper case 302a shown in FIG. 4(a), and the case is hermetically sealed with a solution reagent seal 305, and thereafter, the upper case 301 and the lower case 302 are adhered to each other with an adhesive agent so that the opened bottom surfaces thereof are connected, thereby providing the analysis device 301.
(b) Analysis Initially, the solution reagent seal 305 is removed, and 0.5 µL of blood sample is injected from an injection port 306 of the analysis device 301, and then a case seal 307 is applied to the injection port 306 to hermetically seal the analysis device 301.

Next, the blood sample and the reagent 304 are gently mixed so that the reagent 304 is not applied to the latex reagent 303 held in the upper case 302a, and the solution in this state is left for three minutes. Thereafter, as shown in FIG. 3, the analysis device 301 is set in the analysis system 300, and an absorbance at 550 nm is measured by the measurement unit 310.

Next, as shown in FIG. 4(d), the analysis device 301 is inverted so that the latex reagent 303 in the upper case 302a is mixed and dissolved with the reagent 304, and the solution is left four three minutes. Thereafter, as shown in FIG. 3, the analysis device 301 is set in the analysis system 300, and an absorbance at 550 nm is measured by the measurement unit 310 three minutes after the latex reagent 303 is dissolved.

Although a specific description for the measurement unit 310 will be omitted, the measurement unit 310 irradiates the analysis device 310 with light from the light source 308, and detects the transmitted light by the reception part 309. Since the measurement unit 310 is sufficiently available by using a function of a spectral photometer, a specific description will be omitted. In this third example, cyanmethemoglobin is measured at 540 nm and latex agglutination is measured at 550 nm. This sequence of measurement operations is performed on the blood samples A and B.

Thereafter, the absorbance values obtained as described above are substituted in an analytical curve of cyanmethemoglobin and an analytical curve of latex agglutination inhibition reaction of glycated hemoglobin, which curves have previously been formed by the analysis system 300 using a hemoglobin solution and a glycated hemoglobin solution both having known concentrations, thereby obtaining hemoglobin concentrations and glycated hemoglobin concentrations of the blood samples A and B, respectively.

FIG. 16 is a diagram illustrating the glycated hemoglobin concentrations, the hemoglobin concentrations, and the abundance ratios of glycated hemoglobin, of the blood samples A and B, respectively.

According to FIG. 16, the measurement result of the ratio of glycated hemoglobin which is obtained by the analysis system 300 is very close to the measurement result of the ratio of glycated hemoglobin which is obtained using the automatic glycated hemoglobin analyzer (HLC-723 GHbV) of Tosoh Corporation (refer to FIG. 15), and thereby it is confirmed that the analysis system 300 can perform measurement of accurate hemoglobin concentrations.
Applicability in Industry According to the present invention, since hemoglobin in a sample solution can be speedily and reliably denaturalized, accurate measurement of hemoglobin derivative is realized.

The invention claimed is:

1. A hemoglobin derivative measurement method comprising:
    processing a sample which comprises blood components including erythrocytes, with a reagent composition comprising:
        an oxidizing agent, and
        a nonionic surface-activating agent selected from the group consisting of n-Decyl-β-D-maltoside, n-Nonyl-β-D-thiomaltoside, Sucrose monocaprate, and Sucrose monolaurate,
        whereby the combination of said nonionic surface-activating agent with the oxidizing agent denaturalizes a hemoglobin derivative from the erythrocytes in the sample; and
    detecting the denatured hemoglobin derivative in the sample by performing an immunoassay using an antibody that is specific to a denaturalized site of the hemoglobin derivative.

2. A hemoglobin derivative measurement method as defined in claim 1 wherein said hemoglobin derivative is glycated hemoglobin, and said antibody is specific to a denaturalized site of the glycated hemoglobin.

3. A hemoglobin derivative measurement method as defined in claim 1 further including measuring the hemoglobin included in the sample, and calculating an abundance ratio of the hemoglobin derivative to the hemoglobin.

4. A hemoglobin derivative measurement method as defined in claim 3 wherein said hemoglobin derivative is glycated hemoglobin.

5. A reagent composition for measuring a hemoglobin derivative in a sample which comprises blood components including erythrocytes, said reagent composition comprising:

a nonionic surface-activating agent selected from the group consisting of n-Decyl-β-D-maltoside, n-Nonyl-β-D-thiomaltoside, Sucrose monocaprate, and Sucrose monolaurate;

an oxidizing agent; and an antibody that is specific to a denaturalized site of the hemoglobin derivative from the erythrocytes.

6. A reagent composition as defined in claim 5 wherein said hemoglobin derivative is glycated hemoglobin, and said antibody is specific to a denaturalized site of the glycated hemoglobin.

7. A measurement kit for measuring a hemoglobin derivative in a sample which comprises blood components including erythrocytes, said measurement kit holding:

a reagent composition comprising:

a nonionic surface-activating agent selected from the group consisting of n-Decyl-β-D-maltoside, n-Nonyl-β-D-thiomaltoside, Sucrose monocaprate, and Sucrose monolaurate; and an oxidizing agent;

and an antibody that is specific to a denaturalized site of a hemoglobin derivative from the erythrocytes.

8. A measurement kit as defined in claim 7 wherein said hemoglobin derivative is glycated hemoglobin, and said antibody is specific to a denaturalized site of the glycated hemoglobin.

* * * * *